US007465842B2

(12) United States Patent
Kung et al.

(10) Patent No.: US 7,465,842 B2
(45) Date of Patent: Dec. 16, 2008

(54) ENANTIOSELECTIVE BIOTRANSFORMATION FOR PREPARATION OF PROTEIN TYROSINE KINASE INHIBITOR INTERMEDIATES

(75) Inventors: Pei-Pei Kung, San Diego, CA (US); Carlos Martinez, Oceanside, CA (US); Junhua Tao, San Diego, CA (US)

(73) Assignee: Agouron Pharmaceuticals, Inc., San Diego, CA (US)

(*) Notice: Subject to any disclaimer, the term of this patent is extended or adjusted under 35 U.S.C. 154(b) by 279 days.

(21) Appl. No.: 11/213,025

(22) Filed: Aug. 26, 2005

(65) Prior Publication Data

US 2006/0046287 A1 Mar. 2, 2006

Related U.S. Application Data

(60) Provisional application No. 60/605,118, filed on Aug. 26, 2004.

(51) Int. Cl.
C07C 21/18 (2006.01)
C07C 25/08 (2006.01)
C07C 25/00 (2006.01)
C12P 41/00 (2006.01)

(52) U.S. Cl. .................. 570/126; 570/182; 570/190; 435/280

(58) Field of Classification Search ............ 435/280, 435/290; 570/126, 182, 190
See application file for complete search history.

(56) References Cited

U.S. PATENT DOCUMENTS

| 5,310,666 | A | 5/1994 | Aretz et al. |
| 5,391,495 | A | 2/1995 | Patel et al. |
| 5,457,052 | A | 10/1995 | Tsuboi et al. |
| 5,928,933 | A | 7/1999 | Dicosimo et al. |
| 6,451,587 | B1 | 9/2002 | Burns et al. |
| 6,515,134 | B1 | 2/2003 | Amano et al. |
| 6,638,758 | B2 | 10/2003 | Hansen et al. |
| 6,642,387 | B2 | 11/2003 | Amano et al. |
| 6,703,396 | B1 | 3/2004 | Liotta et al. |
| 6,800,477 | B2 * | 10/2004 | Patel et al. ............ 435/280 |
| 7,230,098 | B2 * | 6/2007 | Cui et al. ............... 544/60 |
| 2005/0009840 | A1 | 1/2005 | Cui et al. |

FOREIGN PATENT DOCUMENTS

| WO | WO 02/077258 | 10/2002 |
| WO | WO 03/093477 | 11/2003 |

OTHER PUBLICATIONS

Adolph, H., et al., "Structural Basis For Substrate Specificity Differences Of Horse Liver Alcohol Dehydrogeanse Isozymes," *Biochemistry*, 2000, 12885-12897, vol. 39.

Allenmark, S., et al., "Chiral Liquid Chromatographic Monitoring Of Asymmetric Carbonyl Reduction By Some Yeast organisms," *Enzyme Microbial Technol.*, 1989, 177-179, vol. 11.
Almsick, A., et al., "Enzymatic Preparation Of Optically Active Cyanohydrin Acetates," *J. Chem. Soc. Chem. Commun.*, 1989, 1391-1393, vol. 18.
Barbieri, C., et al., "Chemo-Enzymatic Synthesis of (R) And (S)-3,4-Dichlorophenylbutanolide Intermediate In The Synthesis Of Sertraline," *Tetrahedron: Asymmetry*, 1999, 3931-3937, vol. 10.
Bauer, A., et al., "Polyvinyl Alcohol-Immobilized Whole-Cell Preparations for The Biotransformation Of Nitriles," *Biotechnology Letters*, 1996, 343-348, vol. 18, No. 3.
Bouzemi, N., et al., "On The Use Of Succinic Anhydride As Acylating Agent For Practical Resolution Of Aryl-Alkyl Alcohols Through Lipase-Catalyzed Acylation," Tetrahedron Letters, 2004, 627-630.
Choi, J., et al., "Aminocyclopentadienyl Ruthenium Complexes As Racemization Catalysts For Dynamic Kinetic Resolution Of Secondary Alcohols At Ambient Temperature," *J. Org. Chem.*, 2004, 1972-1977, vol. 69.
Corey, E., et al., "A Stable And Easily Prepared Catalyst For The Enantioselective Reduction Of Ketones. Applications To Multistep Syntheses," *J. Am. Chem. Soc.*, 1987, 7925-7926, vol. 109.
D'Arrigo, P., et al., "The Effect Of Absorbing Resins On Substrate Concentration And Enantiomeric Excess In Yeast Reduction," *Tetrahedron: Asymmetry*, 1997, 2375-2379, vol. 8, No. 14.
Dale, J., et al., "Nuclear Magnetic Resonance Enantiomer Reagents. Configurational Correlations via Nuclear Magnetic Resonance Chemical Shifts Of Diastereomeric Mandelate, O-Methylmandelate, And αMethoxy- α-Trifluoromethylphenylacetate (MTPA) Esters," *Journal Of The American Chemical Society*, 1973, 512-519, vol. 95, No. 2.
Danda, H., et al., "Preparation Of Optically Active Secondary Alcohols By Combination Of Enzymatic Hydrolysis And chemical Transformation ," *Tetrahedron*, 1991, 8701-8716, vol. 47, No. 41.
Dijksman, A., et al., "Efficient Ruthenium-Catalyzed Racemization Of Secondary alcohols: Application To Dynamic Kinetic Resolution," *Tetrahedron: Asymmetry*, 2002, 879-884, vol. 13.
Gotor, V. "Enzymes In Organic solvents: The Use Of Lipases And (R)-Oxynitrilase For the Preparation Of Products Of Biological Interest," *Molecules*, 2000, 290-292, vol. 5.
Grunwald, J., et al., "Asymmetric Oxidoreductions Catalyzed By Alcohol Dehydrogenase In Organic Solvents,I" *J. Am. Chem. Soc.*, 1986, 6732-6734, vol. 108.

(Continued)

*Primary Examiner*—Irene Marx
*Assistant Examiner*—Susan Hanley
(74) *Attorney, Agent, or Firm*—Bryan C. Zielinski; Galina M. Yakovleva

(57) ABSTRACT

The invention relates to biocatalytic methods for preparing enantiomerically pure stereoisomers of 1-(2,6-dichloro-3-fluorophenyl)ethanol. Disclosed are methods of preparation of the desired (S)-enantiomer, which methods are based on a combination of enzymatic resolution, chemical esterification and chemical hydrolysis with inversion of 1-(2,6-dichloro-3-fluorophenyl)ethyl esters or stereoselective bio-reduction of 2,6-dichloro-3-fluoro-acetophenone with a biocatalyst such as an enzyme or a microorganism. The chiral (S)-enantiomer can be used in the synthesis of certain enantiomerically enriched, ether linked 2-aminopyridine compounds that potently inhibit auto-phosphorylation of human heptocyte growth factor receptor.

16 Claims, No Drawings

OTHER PUBLICATIONS

Itoh, N., et al., "Chiral Alcohol Production By NADH_Dependent Phenylacetaldehyde Reductase Coupled With in situ Regeneration of NADH," *Euro. J. Biochem.*, 2002, 2394-2402, vol. 269.

Jiang, B., et al., "Highly Enantioselective Reduction Of Achiral Ketones With NaBH$_4$/Me$_3$SiC1 Catalyzed By (S)-α, α-Diphenylpyrrolidinemethanol," *Tetrahedron Letters*, 2000, 10281-10283, vol. 41.

Johansson, A., et al., "Horse Liver Alcohol Dehydrogenase Can Accept NADP$^+$ As Coenzyme In High Concentrations Of Acetonitrile," *Eur. J. Biochem.*, 1995, 551-555, vol. 227.

Kim, M., et al., "(S)-Selective Dynamic Kinetic Resolution Of Secondary Alcohols By The Combination Of Subtilisin And An Aminocyclopentadienylruthenium Complex As The Catalysts," *J. Am. Chem. Soc.*, 2003, 11494-11495, vol. 125.

Kirihara, M., et al., "Synthesis Of Optically Active 2,2-Difluorohomoallylalcohols By Lipase-Catalyzed Transesterification," *Tetrahedron: Asymmetry*, 2002, 2283-2289, vol. 13.

Liu, H., et al., "Enantiopure Building Blocks For Chiral Drugs From Racemic Mixtures Of Secondary Alcohols By Combination Of Lipase Catalysis And Mitsunobu Esterification," *Chirality*, 2002, 25-27, vol. 14.

Mathre, D., et al., "A Practical Process For The Preparation Of Tetrahydro-1-methyl-3,3-diphenyl-1$H$,3$H$-pyrrolo[1,2-c]-[1,3,2]oxazaborole-Borane. A Highly Enantioselective Stoichiometrict And Catalytic Reducing Agent," *J. Org. Chem.*, 1983, 2880-2888, vol. 58.

Mitsunobu, O. "The Use Of Diethyl Azodicarboxylate AndTriphenylphosphine In Synthesis And Transformation Of Natural Products," *Synthesis*, 1981, 1-28.

Mukaiyama, T., et al., Optical Interconversion Of Enantiomeric Secondary Alcohols Using 2-Flurobenzothiazolium Salt, *Chemistry Letters*, 1976, 893-896.

Naemura, K., et al., "Enantioselective Acylation Of Primary And Secondary Alcohols Catalyzed By Lipase QL From *Alcaligenes* sp.: A Predictive Active Site Model For Lipase QL To Identify Which Enantiomer Of An Alcohol Reacts Faster In This Acylation," *Tetrahedron: Asymmetry*, 1996, 3285-3294, vol. 7, No. 11.

Naemura, K., et al., "Lipase-Catalyzed Enantioselective Acylation Of Alcohols: A Predictive Active Site Model For Lipase YS To Identify Which Enantiomer Of An alcohol Reacts Faster In This Acylation," *Tetrahedron: Asymmetry*, 1995, 2385-2394, vol. 6, No. 9.

Nakamura, K., et al., "Asymmetric Reduction Of Ketones By The Acetone Powder Of *Geotrichum Candidum*," *Tetrahedron Letters*, 1996, 1629-1632, vol. 37, No. 10.

Nakamura, K., et al., "Asymmetric Reduction Of Ketones By The Acetone Powder Of *Geotrichum Candidum*," *J. Org. Chem*, 1998, 8957-8964, vol. 63.

Nakamura, K., et al., "Recent Developments In Asymmetric Reduction Of Ketones With Biocatalysts," *Tetrahedron: Asymmetry*, 2003, 2659-2681, vol. 14.

Pai, Y., et al., "Resolution Of Homoallylic Alcohols Containing Dithioketene Acetal Functionalities. Synthesis Of Optically Active y-Lactones By A Combination Of Chemical And Enzymatic Methods," *J. Org. Chem.*, 1994, 6018-6025, vol. 59.

Patel, R., et al., "Oxidation Of Secondary Alcohols To Methyl Ketones By Yeasts," *Appied. Environmental Microbiology*, 1979, 219-223, vol. 38, No. 2.

Ponpipom, M., et al., "Enantioselective Cyclization Of Chiral Butane-1,4-Diols To Chiral Tetrahydrofurans: Synthesis Of Chiral Trans-2-(3-Methoxy-5-Methysulfonyl-4-Propoxyphenyl)-5-(3,4,5-Trimethoxyphenyl) Tetrahydrofuran (L-659,989), A Potent Paf-Receptor Antagonist," *Tetrahedron Letters*, 1988, 6211-6214, vol. 29, No. 48.

Prelog, V., et al., "Specification Of The Stereospecificity Of Some Oxido-Reductases By Diamond Lattice Sections," *Pure and Applied Chemistry*, 1964, 119-130, vol. 9, Butterworths, London.

Rotthause, O., et al., "Efficient cyclization Of Squalene Epoxide To Lanosterol With Immobilized Cells Of Baker's Yeast," *Tetrahedron*, 2002, 7291-7293, vol. 58.

Streitwieser, A., et al., "Stereochemistry Of Acetolysis Of Alkyl Sulfonates," *Journal Of The American Chemical Society*, 1965, 3682-3685, vol. 87, No. 16.

Svec, F., et al., "Engineering Aspects Of Carriers For Immobilized Biocatalysts," *Biotechnology And Genetic Engineering Reviews*, 1995, 217-235, vol. 13.

Trost, B., et al., "On The Use Of The *O*-Methylmandelate Ester For Establishment Of Absolute Configuration Of Secondary Alcohols," *J. Org. Chem.*, 1986, 2370-2374, vol. 51.

Vanttinen, E., et al., "Combination Of The Lipase-Catalysed Resolution With The Mitsunobu Esterification In One Pot," *Tetrahedron: Asymmetry*, 1995, 1779-1786, vol. 6, No. 7.

Wang, G., et al., "Synthesis And Cytokine Modulation Properties Of Pyrrolo[2,3-*d*]-4-Pyrimidone Nucleosides," *J. Med. Chem.*, 2000, 2566-2574, vol. 43.

Wang, Y., et al., "Lipase-Catalyzed Irreversible Transesterifications Using Enol Esters As Acylating Reagents: Preparatiave Enantio- And Regioselective Syntheses Of Alcohols, Glycerol Derivatives, Sugars, And Organometallics," *J. Am. Chem. Soc.*, 1988, 7200-7205, vol. 110.

Yazbeck, D., et al., "Automated Enzyme Screening Methods For The Preparation Of Enantiopure Pharmaceutical Intermediates," *Adv. Synth. Catal.*, 2003, 524-532, vol. 345, No. 4.

Zhao, M., et al., "A Convenient And Economical Method For The Preparation Of DIP-Chloride and its Application In The Asymmetric Reduction Of Aralkyl Ketones," *Tetrahedron Letters*, 1997, 2641-2644, vol. 38, No. 15.

Zhu, L., et al., "Applications Of Pig Liver Esterases (PLE) In Asymmetric Synthesis," *Tetrahedron*, 1990, 6587-6611, vol. 46, No. 19.

Zymanczyk-Duda, E., et al., "Stereochemical Control Of Asymmetric Hydrogen Transfer Employing Five Different Kinds Of Fungi In Anhydrous Hexane," *Enzyme Microbial Technology*, 2004, 578-582, vol. 34.

* cited by examiner

US 7,465,842 B2

ENANTIOSELECTIVE BIOTRANSFORMATION FOR PREPARATION OF PROTEIN TYROSINE KINASE INHIBITOR INTERMEDIATES

This application claims the benefit under 35 USC 119(e) of U.S. Provisional Application No. 60/605,118 filed on Aug. 26, 2004, the contents of which is hereby incorporated by reference in its entirety.

FIELD OF THE INVENTION

This invention relates to methods for preparing enantiomerically pure stereoisomers of 1-(2,6-dichloro-3-fluorophenyl)ethanol that are useful intermediates in the synthesis of enantiomerically enriched, ether linked 2-aminopyridine analogues that potently inhibit auto-phosphorylation of human hepatocyte growth factor receptor and therefore may be useful in the treatment of cancer and other hyperproliferative disorders.

BACKGROUND OF THE INVENTION

Strategies to obtain a single enantiomer of a compound have become important in drug discovery because often one enantiomer is an effective drug while the other enantiomer has undesirable biological activity. Ideally, an asymmetric synthesis is designed to produce only the desired enantiomer. Unfortunately, more often than not, an asymmetric synthesis cannot be designed or is prohibitively expensive.

Although 1-(2,6-dichloro-3-fluorophenyl)ethanone was enantioselectively reduced to (1R)-(2,6-dichloro-3-fluorophenyl)ethanol with an enantiomeric purity of 96% enantiomeric excess (ee) using a reducing agent prepared from sodium borohydride, trimethylsilyl chloride and a catalytic amount of (S)-α,α-diphenylpyrrolidinemethanol (Jiang et al. *Tetrahedron Lett.*, 2000, vol. 41, pp. 10281-10283), there is no available chemical synthesis for producing (1S)-(2,6-dichloro-3-fluorophenyl)ethanol, which is an intermediate in the synthesis of certain enantiomerically enriched, ether linked 2-aminopyridine analogues that potently inhibit auto-phosphorylation of human heptocyte growth factor receptor (HGFR or c-MET). Examples of c-MET (HGFR) inhibitors, their synthesis and use, can be found in U.S. patent application Ser. No. 10/786,610, entitled "Aminoheteroaryl Compounds as Protein Kinase Inhibitors", filed Feb. 26, 2004, and corresponding international application PCT/US2004/005495 of the same title, filed Feb. 26, 2004, the disclosures of which are incorporated herein by reference in their entireties.

Our attempts to prepare (1S)-(2,6-dichloro-3-fluorophenyl)ethanol with adequate enantiomeric purity by chiral reduction of 1-(2,6-dichloro-3-fluorophenyl)ethanone using different chemical reagents, for example, (R)-2-methyl-CBS-oxazoborolidine/BH$_3$-dimethylsulfide complex (BMS) (*J. Am. Chem. Soc.* 1987, vol. 109, pp. 7925); sodium borohydride, trimethylsilyl chloride and a catalytic amount of (S)-α,α-diphenylpyrrolidinemethanol (Jiang et al. *Tetrahedron Lett.*, 2000, vol. 41, pp. 10281-10283); oxazoborolidine/BH$_3$-dimethylsulfide complex (BMS) (*J. Org. Chem.* 1993, vol. 58, pp. 2880); and (−)-B-chlorodiisopinocamphenylborane (DIP-Cl) (*Tetrahedron Lett.* 1997, vol. 38, pp. 2641), were unsuccessful.

It is known that enantiomerically pure alcohols can be produced by stereoselective reduction using biocatalysts such as enzymes or microorganisms. For example, phenylacetaldehyde reductase from *Corynebacterium* strain ST-10 has a broad substrate range and reduces various prochiral aromatic ketones and β-ketoesters to yield optically active secondary alcohols with an enantiomeric purity of more than 98% enantiomeric excess (ee). Itoh et al., *Eur. J. Biochem.*, 2002, v. 269, pp. 2394-2402. According to a review on recent developments in the asymmetric reduction of ketones with biocatalysts, for example, for the reduction of ethyl 2-methyl-3-oxobutanoate, *Klebseilla pneumoniae* IFO 3319 out of 450 bacterial strains was found to give the corresponding (2R,3S)-hydroxy ester with >99% ee. K. Nakamura et al. *Tetrahedron: Asymmetry*, 2003, vol. 14, pp. 2659-2681. U.S. Pat. No. 5,310,666 discloses a *Rhodotorula rubra* strain, which reduces pentoxifylline to 100% to give the S-alcohol. U.S. Pat. No. 6,451,587 provides microbial asymmetric reduction processes for preparing the alcohol (R)-2-chloro-1-[6-(2,5-dimethyl-pyrrol-1-yl)-pyridin-3-yl]-ethanol from the ketone 2-chloro-1-[6-(2,5-dimethyl-pyrrol-1-yl)-pyridin-3-yl]-ethanone. U.S. Pat. Nos. 6,642,387 and 6,515,134 disclose preparation of certain optically active hydroxyethyl pyridine derivatives using microbial reduction. U.S. Pat. No. 5,391,495 discloses the stereoselective reduction of certain keto-containing sulfonamide compounds to form the corresponding hydroxyl group-containing compounds utilizing a microorganism or an enzyme capable of catalyzing the reduction. Whole cell biocatalysts were used for reducing 3,4-dichlorophenacylchloride to give the (R)- or (S)-chlorohydrine in high yields and good to high ee. Barbieri at al. *Tetrahedron: Asymmetry*, 1999, vol. 10, pp. 3931-3937. Nonracemic 1-phenylethylalcohol of R and S configuration and of high enantiomeric purity was obtained by bio-reduction of acetophenone in nonaqueous environment—anhydrous hexane. Zymanczyk-Duda et al., *Enzyme Microbiol. Technol.*, 2004, vol. 34, pp. 578-582. WO 02/077258 describes preparation of certain (S)-1-(2,4-substituted-phenyl)ethanol derivatives by microbial reduction. However, the stereoselective microbial and enzymatic reduction of 1-(2,6-dichloro-3-fluorophenyl)ethanone has been unknown.

Alternatively, the mixture of enantiomers can be separated. However, mixtures of enantiomers are difficult, and often impossible, to separate because the physical properties of the enantiomers are identical towards achiral substances and can only be distinguished by their behavior towards other chiral substances. Chromatographic methods using a chiral solid phase have been utilized to separate enantiomeric mixtures, but chiral solid supports are expensive and, typically, the resolution is poor.

An alternative method of separating enantiomeric mixtures is by reacting them with a chiral reagent. In this procedure, the mixture of enantiomers react with the chiral reagent to form diastereomers which are distinguishable from each other on the basis of their properties towards achiral substances, and therefore, can be separated by techniques such as recrystallization or chromatography. This process is time consuming and results in loss of yield because it requires two additional reaction steps (i.e., one reaction to add the chiral auxiliary to the enantiomers and another reaction to remove it after the diasteriomers have been separated).

In some instances, a chiral reagent will react much faster with one enantiomer than with the other enantiomer in the enantiomeric mixture. In this case, the enantiomer which reacts faster can be removed before the other enantiomer is formed. This method also necessitates two additional reaction steps to add the chiral auxiliary and to remove it after the separation.

The methods described above cannot always be applied successfully to a particular system, and when they can be applied, they are often expensive, time consuming and result in loss of yield. Therefore, the need exists for new methods of obtaining a single enantiomer from an enantiomeric mixture.

It is known that chiral resolution of compounds can be achieved by using enzymes, such as esterases, lipases, and proteases or microrganisms. For example, U.S. Pat. No. 6,703,396 describes chiral resolution of a racemic mixture of nucleoside enantiomers based on enzymatic hydrolysis of C5'-nucleoside esters. U.S. Pat. No. 6,638,758 describes the enzymatic resolution of racemic esters of lactams using a biocatalyst, such as an enzyme or a microorganism. U.S. Pat. No. 5,928,933 discloses an enzyme with an enantiomeric excess value of 95% for N-(alkoxycarbonyl)-4-keto-D,L-proline alkyl esters as a result of extensive experiments for reaction specificity of 44 enzymes, including proteases, lipases and esterases. Preparation of certain optically active secondary alcohols by combination of enzymatic hydrolysis and chemical transformation is described, for example, in Danda et al., *Tetrahedron*, 1991, vol. 47, pp. 8701-8716; Vanttinen et al. *Tetrahedron:Asymmetry*, 1995, vol. 6, pp. 1779-1786; and Liu et al., *Chirality*, 2002, vol. 14, pp. 25-27.

Although biocatalysts are very useful for the separation of enantiomeric mixtures, because the selectivity for enantiomers and the optical purity of products may vary depending on the choice of an enzyme or microorganism and the chemical structures of substrates, intensive efforts are required to find combinations of biocatalysts suitable for substrates. Especially, nowhere is found a method for separating enantiomeric 1-(2,6-dichloro-3-fluorophenyl)ethanol esters using a biocatalyst.

SUMMARY OF THE INVENTION

Methods are provided for preparing enantiomerically pure stereoisomers of 1-(2,6-dichloro-3-fluorophenyl)ethanol.

In one embodiment, the present invention provides (1S)-1-(2,6-dichloro-3-fluorophenyl)ethanol that is at least 70% free of (1R)-1-(2,6-dichloro-3-fluorophenyl)ethanol; preferably at least 80% free of (1R)-1-(2,6-dichloro-3-fluorophenyl)ethanol; more preferably at least 90% free of (1R)-1-(2,6-dichloro-3-fluorophenyl)ethanol; and most preferably at least 95% free of (1R)-1-(2,6-dichloro-3-fluorophenyl)ethanol.

In another embodiment, the present invention provides a method of separating enantiomeric 1-(2,6-dichloro-3-fluorophenyl)ethanol esters of formula (I):

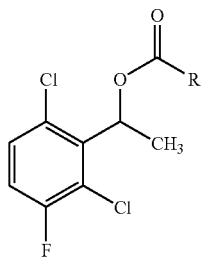

wherein R is hydrogen, $C_1$-$C_{20}$-alkyl, $C_3$-$C_8$-cycloalkyl, $C_6$-$C_{14}$-aryl, $C_7$-$C_{15}$-arylalkyl, $C_1$-$C_{20}$-alkoxy, or $C_1$-$C_{20}$-alkylamino, wherein said hydrocarbon radicals can optionally be monosubstituted or polysubstituted with hydroxyl, formyl, oxy, $C_1$-$C_6$-alkoxy, carboxy, mercapto, sulpho, amino, $C_1$-$C_6$-alkylamino, nitro or halogen, the method comprising the steps of:

contacting the 1-(2,6-dichloro-3-fluorophenyl)ethanol esters of formula (I) with a biocatalyst in an aqueous solution, an organic solvent, or a mixture of organic and aqueous solvents wherein only one enantiomer is selectively hydrolyzed to give an optically active isomer of 1-(2,6-dichloro-3-fluorophenyl)ethanol and an unreacted optically active isomer of 1-(2,6-dichloro-3-fluorophenyl)ethanol ester, and separating the optically active isomer of 1-(2,6-dichloro-3-fluorophenyl)ethanol from the unreacted optically active 1-(2,6-dichloro-3-fluorophenyl)ethanol ester.

In yet another embodiment, the present invention provides a method for preparing (1S)-1-(2,6-dichloro-3-fluorophenyl)ethanol comprising the steps of:

contacting a mixture of enantiomeric 1-(2,6-dichloro-3-fluorophenyl)ethanol esters of formula (I):

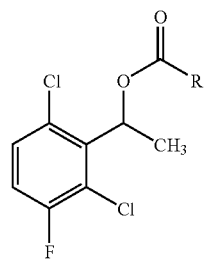

wherein R is hydrogen, $C_1$-$C_{20}$-alkyl, $C_3$-$C_8$-cycloalkyl, $C_6$-$C_{14}$-aryl, $C_7$-$C_{15}$-arylalkyl, $C_1$-$C_{20}$-alkoxy or $C_1$-$C_{20}$-alkylamino, wherein said hydrocarbon radicals can optionally be monosubstituted or polysubstituted with hydroxyl, formyl, oxy, $C_1$-$C_6$-alkoxy, carboxy, mercapto, sulpho, amino, $C_1$-$C_6$-alkylamino, nitro or halogen, with a biocatalyst in an aqueous solution, an organic solvent, or a mixture of organic and aqueous solvents wherein only (R)-enantiomer is selectively hydrolyzed to give a mixture of (1R)-1-(2,6-dichloro-3-fluorophenyl)ethanol and a (1S)-1-(2,6-dichloro-3-fluorophenyl)ethanol ester; and converting the mixture of (1R)-1-(2,6-dichloro-3-fluorophenyl)ethanol and the (1S)-1-(2,6-dichloro-3-fluorophenyl)ethanol ester to (1S)-1-(2,6-dichloro-3-fluorophenyl)ethanol.

Other specific embodiments of this method include those wherein the converting step comprises:

a) reacting (1R)-1-(2,6-dichloro-3-fluorophenyl)ethanol in the mixture of (1R)-1-(2,6-dichloro-3-fluorophenyl)ethanol and the (1S)-1-(2,6-dichloro-3-fluorophenyl)ethanol ester with an organic sulfonyl halide in an aprotic solvent to form a mixture of an organic sulfonic acid ester of (1R)-1-(2,6-dichloro-3-fluorophenyl)ethanol and the (1S)-1-(2,6-dichloro-3-fluorophenyl)ethanol ester;

b) further reacting the organic sulfonic acid ester of (1R)-1-(2,6-dichloro-3-fluorophenyl)ethanol in the mixture of the organic sulfonic acid ester of (1R)-1-(2,6-dichloro-3-fluorophenyl)ethanol and the (1S)-1-(2,6-dichloro-3-fluorophenyl)ethanol ester with an alkali metal salt of an aliphatic carboxylic acid in an aprotic solvent to form a mixture of an aliphatic carboxylic acid ester of (1S)-1-(2,6-dichloro-3-fluorophenyl)ethanol and the (1S)-1-(2,6-dichloro-3-fluorophenyl)ethanol ester; and c) transforming the mixture of the aliphatic carboxylic acid ester of (1S)-1-(2,6-dichloro-3-fluorophenyl)ethanol and the (1S)-1-(2,6-dichloro-3-fluorophenyl)ethanol ester into (1S)-1-(2,6-dichloro-3-fluorophenyl)ethanol.

Yet other specific embodiments of the method include those wherein:

R is methyl;

the biocatalyst is pig liver esterase;

in the reacting step a) the organic sulfonyl halide is methanesulfonyl chloride and the aprotic solvent is pyridine;

in the reacting step b) the alkali metal salt of the aliphatic carboxylic acid is potassium acetate and the aprotic solvent is dimethylformamide;

the transforming step c) is solvolysis in an alcoholic or aqueous solvent in the presence of a basic substance.

Yet other specific embodiments of this method include those comprising the step of selecting the biocatalyst through a high throughput screening process prior to the contacting step.

In another embodiment, the present invention provides a method for preparing an optically active isomer of 1-(2,6-dichloro-3-fluorophenyl)ethanol comprising the step of reducing 1-(2,6-dichloro-3-fluorophenyl)ethanone by a biocatalyst in an enantioselective manner to give the optically active isomer of 1-(2,6-dichloro-3-fluorophenyl)ethanol.

Other specific embodiments of the method include those comprising the step of selecting the biocatalyst through a high throughput screening process prior to the contacting step.

Other specific embodiments of the method include those wherein:

the biocatalyst is horse liver alcohol dehydrogenase or a microorganism of the genus *Rhodotorula*.

Definitions

The term "biocatalyst," as used herein, refers to an enzyme or a microorganism.

The activities of the enzymes used in this invention are expressed in "units". Units are defined as the rate of hydrolysis of p-nitrophenyl propionate as expressed in μmol/min at room temperature.

The term "biotransformation," as used herein, refers to conversion of a substance into other compounds employing an enzyme or microorganism.

The term "bioreduction," as used herein, refers to a process in which electrons are added to an atom or ion (as by adding hydrogen or removing oxygen) employing an enzyme or microorganism; which process always occurs accompanied by oxidation of the reducing agent.

The term "co-factor" or "co-enzyme" means a substance, which activates an enzyme or is necessary for normal activity of an enzyme. The term "co-factor" or "co-enzyme" as used herein, refers to any suitable co-factor or co-enzyme comprising the enzyme reduction system such as, for example, NADH, NADPH, FADH, FMNH, and/or PQQ or any suitable co-factor or co-enzyme, which occurs with the enzyme in the microorganism.

The term "enzyme" includes those enzymes which are known or otherwise obtainable by those skilled in the relevant art and able to accomplish the stereoselective reactions disclosed in the present invention.

The term "enzyme reduction system" means a suitable oxidoreductase enzyme and the reduced form of a co-factor for the oxidoreductase enzyme. The enzyme comprising the enzyme reduction system may be in either free or immobilized form, e.g., in a column or attached to a bead.

The term "enzymatic resolution," "enzymatic process", "enzymatic method" or "enzymatic reaction" denotes a resolution, process, method or reaction of the present invention employing an enzyme or microorganism.

The term "resolution" denotes partial, as well as, preferably, complete separation of the enantiomers of a racemic form.

The term "stereoselective hydrolysis" refers to the preferential hydrolysis of one enantiomer relative to another.

The term "mixture" as used herein in relation to enantiomeric compounds, denotes mixtures having equal (racemic) or nonequal amounts of enantiomers.

The term "enantiomeric excess(es)" is related to the older term "optical purity". In a mixture of a pure enantiomer (S or R) and a racemate, enantiomeric excess is the percent excess of the enantiomer over the racemate. Enantiomeric excess ("ee") can be expressed in the following Equation 1, for example:

$$ee = \frac{[S] - [R]}{[S] + [R]} \qquad \text{Equation 1}$$

$[S]$ = concentration of $S$ enantiomer $[R]$ = concentration of $R$ enantiomer

The term "enantioselectivity value" or "E value" denotes the ratio of specificity constants for each enantiomer of the racemate ($K_{cat}/K_m$) defined below. The E value can be interpreted as the number of times the enzyme is more reactive towards one enantiomer relative to the other (for example, an E value of 50 meaning one enantiomer reacts approximately 50 times faster than the other).

In order to determine the enantioselectivity of the biocatalysts towards a pure enantiomer (S or R), the enantioselectivity value (E) needs to be obtained (Equation 2).

$$E = \frac{K_{catS}/K_S}{K_{catR}/K_R} = \frac{\ln[1-c(1+ee_p)]}{\ln[1-c(1-ee_p)]} = \frac{\ln[1-c(1-ee_s)]}{\ln[1-c(1+ee_s)]} \qquad \text{Equation 2}$$

$K_{catS}$ = first-order enzyme rate constant for enantiomer $S$ $K_S$ = Michaelis constant $c$ = extent of conversion $ee_p$ = enantiomeric excess for product $ee_s$ = enantiomeric excess for substrate For example, for stereoselective hydrolysis of esters by biocatalysts, a program (Ee2 software-University of Graz) can accurately calculate the E value if the enantiomeric excess (ee) of either the alcohol or the ester at one particular enzymatic conversion are known. The ee value can be obtained, for example, from Equation 1. The [S] and [R] data can be obtained, for example, by HPLC.

The term "HPLC" means high pressure liquid chromatography.

The term "RP-HPLC" means reverse phase HPLC.

The term "PLE" means pig liver esterase.

The term "microbial reduction" means the stereoselective reduction as accomplished by the enzyme reduction system, the microbial reductase comprising the enzyme reduction system, the intact microorganism, or any preparation thereof, and the like.

The term "microorganism" includes any intact microorganism or preparation therefrom, including, for example, a broken cell preparation of the microorganism; a dehydrated preparation of the microorganism, e.g., an acetone powder enzymatic preparation; microorganism washed free of, e.g., fermentation medium, culture broth, and the like; microorganism immobilized, e.g., in a column, attached to beads, and the like.

As used herein, the terms "optically pure," "enantiomerically pure," "pure enantiomer," and "optically pure enantiomer" mean a composition that comprises one enantiomer of a compound and is substantially free of the opposite enantiomer of the compound. A typical optically pure compound comprises greater than about 80% by weight of one enantiomer of the compound and less than about 20% by weight of the opposite enantiomer of the compound, more preferably greater than about 90% by weight of one enantiomer of the compound and less than about 10% by weight of the opposite enantiomer of the compound, even more preferably greater than about 95% by weight of one enantiomer of the compound and less than about 5% by weight of the opposite enantiomer of the compound, and most preferably greater than about 97% by weight of one enantiomer of the compound and less than about 3% by weight of the opposite enantiomer of the compound.

The term "suitable mutants" include those microorganisms which are known or otherwise obtainable by those skilled in the relevant art and able, despite such mutation, to accomplish the stereoselective reactions disclosed in the present invention.

The term "halo" or "halogen", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like.

The term "aryl", as used herein, unless otherwise indicated, includes an organic radical derived from an aromatic hydrocarbon by removal of one hydrogen, such as phenyl or naphthyl.

DETAILED DESCRIPTION OF THE INVENTION

The invention relates to biocatalytic methods for preparing enantiomerically pure stereoisomers of 1-(2,6-dichloro-3-fluorophenyl)ethanol. Disclosed are methods of preparation of the desired (S)-enantiomer, which methods are based on a combination of enzymatic resolution, chemical esterification and chemical hydrolysis with inversion of 1-(2,6-dichloro-3-fluorophenyl)ethyl esters or stereoselective bio-reduction of 2,6-dichloro-3-fluoro-acetophenone with a biocatalyst such as an enzyme or a microorganism.

I. Automated Biocatalyst Screening Methods

According to the present invention, an efficient and practical high throughput screening (HTS) process is used to identify the desired biocatalysts from hundreds of potential biocatalysts such as enzymes or microorganisms as well as a number of potential reaction parameters under which they can optimally function. The fact that such parameters, including solvent, solvent content, pH, temperature, time, and cosubstrates, are many times correlated non-linearly makes the screening task even more challenging.

A general HTS protocol that has been validated by a number of global projects within Pfizer is described in Yazbeck et al., *Adv. Synth. Catal.*, 2003, vol. 345, pp. 524-532. Using this approach, hundreds of reactions can be set up and analyzed within days, which otherwise might require weeks using simple vial preparation of reactions. A great advantage gained by using this protocol is that it requires very small amounts of both the biocatalysts, e.g. enzymes, which may be quite expensive, as well as the racemic substrates being screened, which are commonly pharmaceutical intermediates available in limited amounts. The fundamental basis behind this HTS protocol is that enzymes can be stabilized and stored for months in suitable 96-well plates under certain preparative conditions. A second essential requirement is that a number of different analytical instruments be made available to analyze a variety of substrates screened via these 96-well plates. Some of the analytical tools available include high performance liquid chromatography (HPLC), capillary electrophoresis (CE), gas chromatography (GC), UV spectrophotometry, and liquid chromatography coupled with mass spectrometry (LC-MS). Choosing which analytical tool to use depends on the nature of the substrate, mainly its absorbance properties and volatility. Reactivity of the enzyme toward the substrates is usually analyzed first, followed by the analysis of the reactive hits using chiral methods. The same sampled 96-well plate can be used to analyze both reactivity and enantioselectivity. The combination of this screening protocol with statistical optimization algorithms can quickly and efficiently allow the user to predict important conditions and suggest where further optimization should proceed.

II. Preparation of Optically Active 1-(2,6-dichloro-3-fluorophenyl)ethanol by Combination of Enzymatic Resolution and Chemical Transformation A method is provided for the resolution of mixtures of 1-(2,6-dichloro-3-fluorophenyl)ethanol enantiomers.

In one embodiment, the method involves the use of a biocatalyst such as an enzyme or microorganism that preferentially catalyzes a reaction of one enantiomer in a mixture. In the preferred embodiment, the method involves an enzymatic resolution, which is based on stereoselective hydrolysis of 1-(2,6-dichloro-3-fluorophenyl)ethyl esters.

In another embodiment, the reacted enantiomer may be separated from the unreacted enantiomer on the basis of the new difference in physical structure.

In yet another embodiment, the reacted enantiomer may be converted to another enantiomer by chemical transformation with inversion.

In yet another embodiment, the conversion of the reacted enantiomer to another enantiomer may be performed in the mixture of the reacted enantiomer and the unreacted enantiomer.

II(a). Enzymatic Resolution Based on Stereoselective Hydrolysis of 1-(2,6-Dichloro-3-Fluorophenyl)Ethyl Esters A method of stereoselective hydrolysis is provided for the enzymatic resolution of mixtures of 1-(2,6-dichloro-3-fluorophenyl)ethanol enantiomers. Given the disclosure herein, one of skill in the art will be able to choose, using the high throughput screening (HTS) process described above, an enzyme or microorganism that is selective for the 1-(2,6-dichloro-3-fluorophenyl)ethyl ester enantiomer of choice or selective for the undesired enantiomer, as a method of eliminating it, by selecting one of the enzymes or microorganisms discussed below or by systematic evaluation of other known enzymes or microorganisms. Given this disclosure, one of skill in the art will also know how to modify the substrate as necessary to attain the desired resolution. Through the use of chiral NMR shift reagents, polarimetry, or chiral HPLC, the optical enrichment of the recovered ester or alcohol can be determined. See, for example, *J. Am. Chem. Soc.* 1973, v. 95, p. 512; Trost et al., *J. Org. Chem.* 1986, v. 51, pp. 2370-2374; *J. Org. Chem.* 1998, v. 63, p. 8957; *Tetrahedron: Asymmetry* 1995, v. 6, p. 2385; *Tetrahedron: Asymmetry* 1996, v. 7, p. 3285.

The following examples further illustrate the use of enzymes or microorganisms to resolve racemic mixtures of enantiomers. Other known methods of resolution of racemic mixtures can be used in combination with the method of resolution disclosed herein. See, for example, Roger A Sheldon, *Chirotechnology: industrial synthesis of optically active compounds*, New York, Marcel Dekker, 1993. All of these modifications are considered within the scope of the invention.

In this embodiment, the method includes reacting the hydroxyl group of a mixture of 1-(2,6-dichloro-3-fluorophenyl)ethanol enantiomers with an acyl compound to form esters in which 1-(2,6-dichloro-3-fluorophenyl)ethanol is in the "carbinol" end of the ester. The mixture of 1-(2,6-dichloro-3-fluorophenyl)ethyl ester enantiomers is then treated with a biocatalyst that preferentially cleaves, or hydrolyses, one of the enantiomers and not the other.

An advantage of this method is that it can be used to resolve a wide variety of 1-(phenyl)ethanols that are optionally substituted in the carbinol moiety. The broad applicability of this method can reside in part on the fact that although the carbinol portion of the ester can play a role in the ability of a biocatalyst to differentiate enantiomers, the major recognition site for these biocatalysts can be in the carboxylic acid portion of the ester. Further, one may be able to successfully extrapolate the results of one biocatalyst/substrate study to another, seemingly different system, provided that the carboxylic acid portions of the two substrates are the same or substantially similar.

Still another advantage of this method is that the separation of the unhydrolysed enantiomer and the hydrolysed enantiomer from the reaction mixture can be quite simple. The unhydrolysed enantiomer can be more lipophilic than the hydrolysed enantiomer and can be efficiently recovered by simple extraction with one of a wide variety of nonpolar organic solvents or solvent mixtures, for example, hexane and hexane/ether. The less lipophilic, more polar hydrolysed enantiomer can then be obtained by extraction with a more polar organic solvent, for example, ethyl acetate, or by lyophilization, followed by extraction, for example, with ethanol or methanol.

The enzyme or microorganisms may be used alone or in combination. Depending upon the type of enzyme or microorganism used, either one of the optical isomers of the ester is predominantly hydrolyzed to give the optically active alcohol. Either one of the optical isomers may be obtained by the selection of a suitable enzyme or microorganism.

With the proper matching of enzyme and substrate, conditions can be established for the isolation of either 1-(2,6-dichloro-3-fluorophenyl)ethanol enantiomer. The desired enantiomer can be isolated by treatment of the racemic mixture with an enzyme that hydrolyses the desired enantiomer (followed by extraction of the polar hydrolysate with a polar solvent) or by treatment with an enzyme that hydrolyses the undesired enantiomer (followed by removal of the undesired enantiomer with a nonpolar solvent).

II(b). Biocatalysts

In one embodiment of the present invention, the method of enzymatic resolution employs an enzyme as a biocatalyst for stereoselective hydrolysis of 1-(2,6-dichloro-3-fluorophenyl)ethyl esters. Examples of enzymes that catalyze the hydrolysis of esters include, but are not limited to, esterases, lipases and proteases (substillisin and α-chymotrypsin). The enzyme may be any enzyme obtainable from animals, plants, microorganisms, etc. The enzyme may be employed in any conventional form such as in a purified form, a crude form, a mixture with other enzymes, a microbial fermentation broth, a fermentation broth, a microbial body, a filtrate of fermentation broth, and the like, either solely or in combination. In addition, the enzyme or microbial body may be immobilized on a resin.

Specific examples of the enzyme are those obtained from animal and plants useful in the present invention including, but not limited to, cow liver esterase, pig liver esterase, pig pancreas esterase, horse liver esterase, dog liver esterase, pig phosphatase, amylase obtainable from barley and potato and lipase obtainable from wheat. For example, applications of pig liver esterase in asymmetric synthesis are described in *Tetrahedron*, 1990, vol. 46, pp. 6587-6611; *Enzyme Catalysis in Organic Synthesis*, 2nd Ed., Wiley-VCH 2002, vol. II, pp. 384-397. Other examples are hydrolases obtained from such microorganisms as *Rhodotorula, Trichoderma, Candida, Hansenula, Pseudomonas, Bacillus, Achromobacter, Nocardia, Chromobacterium, Flavobacterium, Rhizopus, Mucor, Aspergillus, Alkaligenes, Pediococcus, Kiebsiella, Geotrichum, Lactobaccilus, Cryptococcus, Pichia, Aureobasidium, Actinomucor, Enterobacter, Torulopsis, Corynebacterium, Endomyces, Saccaromyces, Arthrobacter, Metshnikowla, Pleurotus, Streptomyces, Proteus, Gliocladium, Acetobacter, Helminthosporium, Brevibacterium, Escherichia, Citrobacter, Absidia, Micrococcus, Microbacterium, Penicillium* and *Schizophyllium* as well as from lichen and algae.

Exemplary, commercially available enzymes suitable for use in the present invention include esterases such as, for example, pig liver esterase (Biocatalytics Inc), lipases such as Amano PS-30 (*Pseudomonas cepacia*), Amano GC-20 (*Geotrichum candidum*), Amano APF (*Aspergillus niger*), Amano AK (*Pseudomonas* sp.), *Pseudomonas fluorescens* lipase (Biocatalyst Ltd.), Amano Lipase P30 (*Pseudomonas* sp.), Amano P (*Pseudomonas fluorescens*), Amano AY-30 (*Candida cylindracea*), Amano N (*Rhizopus niveus*), Amano R (*Penicillium* sp.), Amano FAP (*Rhizopus oryzae*), Amano AP-12 (*Aspergillus niger*), Amano MAP (*Mucor melhei*), Amano GC-4 (*Geotrichum candidum*), Sigma L-0382 and L-3126 (porcine pancrease), Lipase OF (Sepracor), Esterase 30,000 (Gist-Brocarde), KID Lipase (Gist-Brocarde), Lipase R (*Rhizopus* sp., Amano), Sigma L-3001 (Wheat germ), Sigma L-1754 (*Candida cytindracea*), Sigma L-0763 (*Chromobacterium viscosum*) and Amano K-30 (*Aspergillus niger*). Additionally, exemplary enzymes derived from animal tissue include chymotrypsin and pancreatin from pancreas such as porcine pancreatic lipase (Sigma). Two or more, as well as a single, enzyme may be employed when carrying out the process of the present invention.

In addition, enzymes, which are serine carboxypeptidases can be used. These enzymes are derived from *Candida lipolytica, Saccharomyces cerevisiae*, wheat (*Triticum aestivum*) and *Penicillium janthinellum*. Commercially available cross-linked enzyme crystals may also be used such as from Altus Biologics, Inc. (e.g., ChiroCLEC-CR, ChiroCLEC-PC, ChiroCLEC-EC).

The present invention is also directed to the use of thermostable esterases and genetically engineered esterases for the resolution of the esters. These enzymes, commercially available from ThermoGen, Inc., are especially suitable for use in industrial processes and are easy to use. In addition to functioning at a wide range of temperatures including higher temperatures, these thermostable enzymes possess an increased shelf life which improves handling. The enzymes are also able to endure harsh, non-biological conditions (pH, salt concentrations, etc.) usually associated with industrial processes because of their stability under operational conditions. They can be immobilized for reuse in multiple applications, improving the cost-effectiveness of the process.

During the isolation of the products after enzymatic resolution, the enzymes are frequently exposed to traces of organic solvents. In addition, some enzymatic resolutions are found to work best under a mixture of aqueous and organic solvents or in organic solvents alone. The esterase enzymes of the present invention are more tolerant to denaturing by many organic solvents compared to conventional enzymes which allows longer operational half lives. Most of the esterase enzymes are produced using genetic engineering techniques of gene cloning which ensures the purity of these enzymes and the ease of process controls during scale up. Instead of isolated enzymes, there may also be employed a microorganism which can produce any enzyme discussed above.

In another embodiment of the present invention, the method of enzymatic resolution employs a microorganism as a biocatalyst for stereoselective hydrolysis of 1-(2,6-dichloro-3-fluorophenyl) ethyl esters. Specific examples of the microorganisms useful in the present invention include, but are not limited to, Rhodotorula minuta, Rhodotonula rubra, Candida krusei, Candida cylindracea, Candida tropicalis, Candida utilus, Pseudomonas fragi, Pseudomonas putida, Pseudomonas fluorescens, Pseudomonas aeruginosa, Rhizopus chinensis, Mucor pusillus, Aspergillus niger, Alkaligenes faecalis, Torulopsis emobii, Bacillus cereus, Bacillus subtilis, Bacillus pulmilus, Bacillus subtilis var. niger, Citrobacter freundii, Micrococcus varians, Micrococcus luteus, Pediococcus acidlactici, Klebsiella pneumoriae, Absidia hyalospora, Geotrichun candidum, Schizophyllum commune, Nocardia uniformis subtsuyanarenus, Nocardia uniformis, Chromobacterium chocolatum, Hansenula anomala var. ciferrii, Hansenula anomala, Hansenula polymorpha, Achromobacter lyticus, Achromobacter parvulus, Achromobacter sinplex, Torulopsis candida, Corynebacterium sepedonicum, Endomyces geotrichum, Saccaromyces carryisial, Arthrobacter globiformis, Streptomyces grisens, Micrococcus luteus, Enterobacter cloacae, Corynebacterium ezui, Lacto bacillus casei, Cryptococcus albidus, Pichia polimorpha, Penicillium frezuentans, Aureobasidium pullulans, Actinomucor elegans, Streptomyces grisens, Proteus vulgaris, Gliocladium roseum, Gliocladium virens, Acetobacter aurantius, Helminthosporium sp. Chromobacterium iodinum, Chromobacterium violaceum, Flavobacterium lutescens, Metschnikowia pulcherrima, Pleurotus ostreatus, Brevibacterium ammoniagenes, Brevibacterium divaricatum, Escherichia coli, Rodotolura minuta var. texensis, Trichoderma longibrachiatum, Mucor javanicus, Flavobacterium arbonescens, Flavobacterium heparinum, and Flavobacterium capsulatum.

The enzymes and/or microorganisms used in the present invention may be in crude form or in an immobilized form. They can be immobilized on various solid supports without loss of stereospecificity or change in stereo selectivity. The solid supports can be inert absorbents to which the enzyme is not covalently bonded. Instead the enzyme is absorbed such as by interactions of hydrophobic or hydrophilic portions of a protein with like regions of the inert absorbent, by hydrogen bonding, by salt bridge formation, or by electrostatic interactions. Inert absorbent materials include, but are not limited to, synthetic polymers (e.g. polystyrene, poly-(vinylalcohol), polyethylene and polyamides), mineralaceous compounds (e.g. diatomaceous earth and Fuller's earth), or naturally occurring polymers (e.g. cellulose). Specific examples of such materials include Celite 545 diatomaceous earth, Abelite XAD-8 polymeric resin beads and polyethylene glycol 8000.

The enzyme may also be immobilized on the support to which the enzyme is covalently bonded (e.g., oxirane-acrylic beads and glutaraldehyde activated supports). Specific examples include Eupergit C oxirane-acrylic beads and glutaraldehyde activated Celite 545. Other possible immobilizing systems are well known and are readily available to those skilled in the art of enzyme immobilization.

Instead of conventional immobilization methods described above, the enzymes can also be conveniently recycled for reuse by simply precipitating out the used enzymes with ammonium sulfate. The precipitated enzyme-ammonium sulfate can be used directly in the next enzymatic hydrolysis. Salts are commonly used in purification of enzymes. They generally protect the protein enzymes by reducing solvent activity. For example, ammonium sulfate, potassium sulfate, potassium phosphate, sodium chloride, etc., can be used in recovering the enzyme activity.

The enzyme or microorganisms may be used alone or in combination. Depending upon the type of enzyme or microorganism used, either one of the optical isomers of the ester is predominantly hydrolyzed to give the optically active alcohol. Either one of the optical isomers may be obtained by the selection of a suitable enzyme or microorganism.

II(c). Substrates

The most effective acyl group to be used to esterify 1-(2, 6-dichloro-3-fluorophenyl)ethanol can be determined without undue experimentation by evaluation of a number of homologs using the selected enzyme system. Non-limiting examples of acyl groups that can be evaluated for use with a particular enzyme or microorganism include alkyl carboxylic acids and substituted alkyl carboxylic acids, including acetic acid, propionic acid, butyric acid, and pentanoic acid. With certain enzymes or microorganisms, it may be preferred to use an acyl compound that is significantly electron-withdrawing to facilitate hydrolysis by weakening the ester bond. Examples of electron-withdrawing acyl groups include α-haloesters such as 2-chloropropionic acid, 2-chlorobutyric acid, and 2-chloropentanoic acid. α-Haloesters are excellent substrates for lipases. In addition, the use of succinic anhydride as acylating agent for practical resolution of aryl-alkyl alcohols through lipase-catalyzed acylation has been reported in Bouzemi et al. *Tetrahedron Lett.*, 2004, vol. 45, pp. 627-630.

The different methods of esterification known in the art may be used for preparing the 1-(2,6-dichloro-3-fluorophenyl)ethanol esters substrates. See, for example, *J. Chem. Soc. Chem. Commun.* 1989, vol. 18, p. 1391; *J. Org. Chem.* 1994, vol. 59, p. 6018.

II(d). Reaction Conditions for Enzymatic Hydrolysis

The enzymatic hydrolysis of the present invention may be carried out by contacting the 1-(2,6-dichloro-3-fluorophenyl) ethyl esters with the enzyme or microorganism, usually in an aqueous buffer medium with good agitation.

The buffer medium may be inorganic acid salt buffers (e.g. potassium dihydrogen phosphate, sodium dihydrogen phosphate), organic acid salt buffers (e.g. sodium citrate), or any other suitable buffer. The concentration of the buffer may vary from 0.005 to 2 M, preferably from 0.005 to 0.5 M and will depend on the specific 1-(2,6-dichloro-3-fluorophenyl) ethyl ester and the enzyme or microorganism used.

Enzymatic hydrolyses performed under heterogeneous conditions can suffer from poor reproducibility. Therefore, it is preferred that the hydrolysis be performed under homogeneous conditions. Depending on the solubility of the 1-(2,6-dichloro-3-fluorophenyl)ethyl esters, homogeneity can be achieved through the use of surfactants. Preferred surfactants include but are not limited to non-ionic surfactants such as alkylaryl polyether alcohols. A preferred surfactant is octylphenoxy polyethoxyethanol, commercially available as Triton X-100 (Sigma Chemical Company). An effective amount of a surfactant is used. Typical amounts can vary from 0.05% to about 10% (v/v).

However, these surfactants not only assist in dissolving the starting material, they also enhance the aqueous solubility of the product. Therefore, although the enzymatic reaction can proceed more effectively with the addition of a non-ionic surfactant than under heterogeneous conditions, the isolation of both the recovered starting material and the product can be made more difficult. The product can be isolated with appropriate chromatographic and chemical (e.g., selective salt formation) techniques.

It is sometimes preferable to add an effective amount of an organic cosolvent to increase product solubility to facilitate the reaction. Examples of co-solvents include but are not limited to acetonitrile, THF, DMSO, DMF, alcohols, etc. Effective amounts of a co-solvent include from 1% to 30% (v/v) depending on the specific 1-(2,6-dichloro-3-fluorophenyl)ethyl ester and the enzyme or microorganism used.

The enzymatic hydrolyses are typically carried out with a catalytic amount of the enzyme in an aqueous buffer that has a pH that is close to the optimum pH for the enzyme in question. As the reaction proceeds, the pH drops as a result of liberated carboxylic acid. Aqueous base can be added to maintain the pH near the optimum value for the enzyme. The progress of the reaction can be easily determined by monitoring the change in pH and the amount of base needed to maintain pH.

The pH of the buffers or the pH of the reaction is normally from 4 to 10, preferably from 5 to 9, most preferably from 7 to 8. The reaction temperature may vary from 0 to 100° C. and will depend on the specific 1-(2,6-dichloro-3-fluorophenyl) ethyl ester and the enzyme or microorganism used. The reaction time is generally from 1 hour to 70 hours and will depend on the specific 1-(2,6-dichloro-3-fluorophenyl)ethyl ester, enzyme concentration and the enzyme or microorganism used. Normally, the enzymatic hydrolysis is allowed to proceed for a period sufficient to generate a satisfactory quantity of the desired ester or 1-(2,6-dichloro-3-fluorophenyl)ethanol in satisfactory optical purity. As the reaction progresses, the amount of desired ester or alcohol and its optical purity can be monitored by HPLC and chiral HPLC. Normally, the conversion is carried to approximately 50%, after which the alcohol and the esters may be obtained in good yields after isolation.

The amount of enzyme used can vary widely from 5 units to 12,000 units of enzyme per mole of starting material. The amount of enzyme needed will depend on the temperature, the specific 1-(2,6-dichloro-3-fluorophenyl)ethyl ester, the enzymes and/or microorganism used, and the desirable reaction time. It may also be desirable to use a large amount of enzymes in some cases to ensure a practically short reaction time, especially when the enzymes are immobilized and can be reused for many turnovers. The concentration of the ester substrate may be from 0.1 g/L to 500 g/L and depends on the specific 1-(2,6-dichloro-3-fluorophenyl)ethyl ester and the enzyme and/or microorganism used.

II(e). Product Isolation

The desired products, the optically pure (or enriched) unreacted ester and the optically pure (or enriched) alcohol can be isolated from the hydrolysis mixture using conventional methods such as extractions, acid-base extractions, filtration, chromatography, crystallization or combinations thereof. Andreas Liese, et al, *Industrial Biotransformations*, Weinheim: WILEY-VCH, 2000. The recovered enzyme or microorganism may be recycled as described above.

II(f). Enantiomeric Conversion Based on Esterification and Chemical Hydrolysis with Inversion According to the present invention, either 1-(2,6-dichloro-3-fluorophenyl)ethanol enantiomer may be converted to the other 1-(2,6-dichloro-3-fluorophenyl)ethanol enantiomer if desired. This conversion may be performed, for example, by a nucleophilic substitution reaction at C-1 accompanied by a steric inversion. Such reaction can be conducted with the use of a nucleophilic reagent.

Methods for the conversion of the optically active alcohol to the corresponding enantiomer include, but are not limited to, the following methods.

For example, one method comprises converting the hydroxyl group on the asymmetric carbon atom of the particular enantiomer into an organic sulfonic acid ester, preferably a methanesulfonic acid ester or a p-toluenesulfonic acid ester, which is directly converted into the other enantiomer by nucleophilic substitution and inversion of configuration via one of their carboxylic acid esters and its subsequent solvolysis or hydrolysis. The sulfonic acid esters are prepared by known methods by reaction of either 1-(2,6-dichloro-3-fluorophenyl)ethanol enantiomer with organic sulfonyl halides, preferably methanesulfonyl chloride and p-toluenesulfonyl chloride, in aprotic solvents, preferably pyridine and dichloromethane, if appropriate in the presence of a base, such as triethylamine.

A method comprising esterifying an optically active alcohol with fuming $HNO_3$ or mesyl chloride to nitrate or mesylate, and hydrolyzing the resultant nitrate or mesylate with a steric inversion under neutral (in the presence of 0.7 to 2.0 equivalent of $CaCO_3$ or NaOAc), basic ($K_2CO_3$) or acidic conditions (2.5% aqueous $H_2SO_4$ or 2.5% aqueous $HNO_3$) is described, for example, in Danda et al., *Tetrahedron*, 1991, vol. 47, pp. 8701-8716; and Wang et al., *J. Med. Chem.*, 2000, vol. 43, No. 13, pp. 2566-2574.

A method comprising converting an optically active alcohol to a sulfonic acid ester such as p-toluenesulfonic acid ester, allowing an organic acid salt such as tetraethylammonium acetate and sodium acetate (and acetic acid) to react with the resulting sulfonic acid ester to sterically invert to the corresponding organic acid ester, and hydrolyzing the resultant organic acid ester is described, for example, in *J. Am. Chem. Soc.*, 1965, v. 87, p. 3682; and *J. Chem. Soc.*, 1954, p. 965.

A method comprising esterifying an optically active alcohol to a carboxylic acid ester such as trichloroacetic acid ester, and hydrolyzing the resultant carboxylic acid ester, in a water-ether solvent such as 75% $H_2O$-dioxane is described, for example, in *Chem. Lett.*, 1976, p. 893.

Another example is the Mitsunobu reaction, which reaction comprises reacting an optically active alcohol with an organic acid in the presence of triarylphosphine (for example, triphenylphosphine) and an azodicarboxylic acid ester such as diethyl azodicarboxylate to form the sterically inverted corresponding organic acid ester, and hydrolyzing the resulting ester. The organic acid includes, for example, formic acid, acetic acid, trichloroacetic acid, trifluoroacetic acid, benzoic acid and the like. The formation of the organic acid ester may be conducted, for example, at a temperature of about −60° C. to 60° C. The reaction may be carried out in an inert solvent such as an aromatic hydrocarbon (for example, benzene, toluene, etc.) and an ether (for example, tetrahydrofuran, etc.). The proportions of trialkylphosphine, organic acid and azodicarboxylic acid ester based on 1 mole of an optically active alcohol are respectively about 0.7 to 2.0 moles. The hydrolysis of the organic acid ester can be conducted by a conventional manner such as acidic or basic hydrolysis. See, for example, *Synthesis*, 1981, p. 1; Danda et al., *Tetrahedron*, 1991, vol. 47, pp. 8701-8716; Vanttinen et al. *Tetrahedron: Asymmetry*, 1995, vol. 6, pp. 1779-1786; and Liu et al., *Chirality*, 2002, vol. 14, pp. 25-27.

II(g). Combination of Enzymatic Hydrolysis, Esterification and Chemical Hydrolysis with Inversion One major limitation of the enzymatic resolution method is that the maximum yield is 50% based on the racemate. As a method to overcome this limitation, combination of enzymatic hydrolysis, esterification and chemical hydrolysis with inversion may be used. See, for example, Danda et al., *Tetrahedron*, 1991, vol. 47, pp. 8701-8716; Vanttinen et al. *Tetrahedron:Asymmetry*, 1995, vol. 6, pp. 1779-1786; and Liu et al., *Chirality*, 2002, vol. 14, pp. 25-27.

According to the present invention, a crude mixture of the optically pure (or enriched) unreacted ester and the optically pure (or enriched) alcohol obtained by the enzymatic hydrolysis, can be subject to enantiomeric conversion based on esterification and chemical hydrolysis with inversion in one pot according to the procedures described above.

Depending on the 1-(2,6-dichloro-3-fluorophenyl)ethyl ester substrates, an appropriate enzyme or microorganism can be employed for enzymatic hydrolysis and appropriate conditions for chemical hydrolysis can be chosen. For example, a crude mixture of the unreacted (1S)-1-(2,6-dichloro-3-fluorophenyl)ethyl ester and the reacted (1R)-1-(2,6-dichloro-3-fluorophenyl)ethanol without separation can be esterified with mesyl chloride as described in Danda et al., *Tetrahedron*, 1991, vol. 47, pp. 8701-8716; and Wang et al., *J. Med. Chem.*, vol. 43, pp. 2566-2574. Successively, a resultant crude mixture of the corresponding (1R)-1-(2,6-dichloro-3-fluorophenyl)ethyl mesylate and (1S)-1-(2,6-dichloro-3-fluorophenyl)ethyl ester without purification can be hydrolyzed to afford (1S)-1-(2,6-dichloro-3-fluorophenyl)ethanol, with inversion of (1R)-1-(2,6-dichloro-3-fluorophenyl)ethyl mesylate and retention of (1S)-1-(2,6-dichloro-3-fluorophenyl)ethyl ester. In a specific embodiment, the 1-(2,6-dichloro-3-fluorophenyl)ethyl ester substrate is 1-(2,6-dichloro-3-fluorophenyl)ethyl acetate. In a specific embodiment, the enzyme is pig liver esterase.

The methods for conversion of (1R)-1-(2,6-dichloro-3-fluorophenyl)ethanol to (1S)-1-(2,6-dichloro-3-fluorophenyl)ethanol can also be applied to the conversion of (S)-enantiomer to (R)-enantiomer.

II(h). Racemization and Application to Dynamic Kinetic Resolution

Either of the optically pure (or enriched) unreacted ester and the optically pure (or enriched) alcohol can be racemized if desired. The optically pure (or enriched) unreacted ester can be racemized by heating in the appropriate base under appropriate conditions. Alternatively, the optically pure (or enriched) unreacted ester can be racemized by heating in acid in the presence of an alcohol under appropriate conditions. The optically pure (or enriched) unreacted alcohol can also be racemized and converted to the racemic esters by heating in acid under appropriate conditions. In this manner, excellent yields can be achieved of either the optically pure (or enriched) unreacted ester or the optically pure (or enriched) alcohol by this combination of stereoselective enzymatic hydrolysis and racemization techniques.

For example, a method of dynamic kinetic resolution (or second-order asymmetric transformations) can be used for secondary alcohols, in which the alcohols are continuously racemized with metal catalysts, such as ruthenium-based catalytic systems, during an enzymatic resolution. Dijksman et al., *Tetrahedron: Asymmetry*, 2002, vol. 13, pp. 879-884; Kim et al., *J. Am. Chem. Soc.*, 2003, vol. 125, pp. 11494-11495; Choi et al., *J. Org. Chem.*, 2004, vol. 69, 1972-1977.

II(i). Enzyme-Catalyzed Acylation

Enzymatic reactions have proved to be a convenient method for obtaining optically enriched compounds from their racemic form by kinetic resolution. C.-H. Wong and G. M. Whitesides, *Enzymes in Synthetic Organic Chemistry*, Pergamon, Oxford (1994); K. Faber, *Biotransformations in Organic Chemistry*, Springer, Berlin (1995); Gotor, Vicente. "Enzymes In Organic Solvents: The Use Of Lipases And (R)-Oxynitrilase For The Preparation Of Products Of Biological Interest." *Molecules* [Electronic Publication] 2000, vol. 5, pp. 290-292.

For example, alcohols can be resolved through lipase-catalyzed transesterification (acylation) with enol esters in a generally irreversible reaction. Y. F. Wang, J. J. Lalonde, M. Momongan, D. E. Bergbreiter and C.-H. Wong. *J. Am. Chem. Soc.* 1988, vol. 110, pp. 7200-7205. However, to be of preparative interest such a process requires (i) a high enantioselectivity factor E, (ii) easy separation of the unreacted substrate (alcohol) from the product (ester). It was shown that the use of a cyclic anhydride as an acylating agent offers a convenient solution to this requirement. Bouzemi et al. *Tetrahedron Lett.*, 2004, vol. 45, pp. 627-630. The acid-ester produced can be readily separated from the unreacted alcohol by a simple aqueous base-organic solvent liquid-liquid extraction. Moreover, since the separation of these compounds is easy even for very different amounts of product and unreacted substrate, alcohols of high enantiomeric purity can be obtained from a racemic substrate even in the cases of low E values, provided the acylation is carried out to high conversion.

Reactions can be carried out using racemic substrate dissolved in diethyl ether. Vinyl or isopropenyl acetates (2 equivalents) or succinic anhydride (1 equivalent), can be then added, followed by the enzyme. For example, commercially available lipases such as *Pseudomonas fluorescens* lipase (PFL) and *Candida antarctica* lipase B (CAL B), an immobilized enzyme can be used. The resulting mixture can be stirred at room temperature for the appropriate time to reach approximately 50% conversion. With enol esters as acylating agents, the unreacted alcohol and the acetate produced were separated by silica-gel flash chromatography. The ee's of both compounds could be measured before separation through analysis using chiral HPLC. With succinic anhydride as acylating agent, the unreacted alcohol, for example, (S)-alcohol, and the (R)-monosuccinate produced can be separated by aqueous base-organic solvent liquid-liquid extraction. The aqueous phase can be made alkaline with sodium hydroxide and the resulting (R)-alcohol extracted with an organic solvent. Enantiomeric excesses of the unreacted (S)-enriched-alcohol and the (R)-enriched-alcohol produced can be evaluated, for example, by chiral HPLC.

III. Enantioselective Bio-Reduction of 1-(2,6-dichloro-3-fluorophenyl)ethanone The present invention provides a method for preparing an optically active isomer of 1-(2,6-dichloro-3-fluorophenyl)ethanol comprising the step of reducing 1-(2,6-dichloro-3-fluorophenyl)ethanone by a biocatalyst in an enantioselective manner in an aqueous solution, an organic solvent, or a mixture of organic and aqueous solvents to give the optically active isomer of 1-(2,6-dichloro-3-fluorophenyl)ethanol. Given the disclosure herein, one of skill in the art will be able to choose, using the high throughput screening (HTS) process described above, an enzyme or microorganism which selectively reduces 1-(2,6-dichloro-3-fluorophenyl)ethanone to either enantiomer of 1-(2,6-dichloro-3-fluorophenyl)ethanol, by selecting of one of the enzymes or microorganisms discussed herein or by systematic evaluation of other known enzymes or microorganisms. Those skilled in the art will understand based upon the description provided herein how to select the conditions of the bio-reduction reaction such that the desired stereoselectivity is achieved. Through the use of chiral NMR shift reagents, polarimetry, or chiral HPLC, the optical enrichment of the recovered alcohol can be determined. See, for example, *J. Am. Chem. Soc.* 1973, v. 95, p. 512; Trost et al., *J. Org. Chem.* 1986, v. 51, pp. 2370-2374; *J. Org. Chem.* 1998, v. 63, p. 8957; *Tetrahedron: Asymmetry* 1995, v. 6, p. 2385; *Tetrahedron: Asymmetry* 1996, v. 7, p. 3285.

The desired enantiomer, for example, (1S)-1-(2,6-dichloro-3-fluorophenyl)ethanol, is then optionally isolated from any residual substrate and other reaction components using methods well known in the art (e.g., the reaction mixtures can be extracted with a suitable solvent such as MeOH and analyzed by RP-HPLC; the corresponding alcohol can be separated from the other organics by flash chromatography, and the purified alcohol can be analyzed by chiral HPLC, see, e.g., Allenmark et al. *Enzyme Microbial Technol.*, 1989, vol. 11, pp. 177-179), prior to its preferred use as an intermediate in synthesis of certain enantiomerically enriched, ether linked 2-aminopyridine analogues that potently inhibit auto-phosphorylation of human heptocyte growth factor receptor, as described in EXAMPLE 3 herein.

Generally, only a very small quantity (e.g., from about 1% ee to about 5% ee), if any, of the undesired enantiomer is produced by the stereoselective bio-reduction processes of this invention. Yet, where so desired, the amount of the desired enantiomer can be substantially separated from the amount of the undesired enantiomer, for example, by crystallization.

The methods of the present invention are readily carried out. Thus, an enzyme or microorganism is either incubated (the enzyme, broken cell preparation, dehydrated preparation, or any other suitable preparation of the microorganism) or fermented (intact microorganism) in the presence of an amount of the substrate, 1-(2,6-dichloro-3-fluorophenyl)ethanone, to produce a greater amount of the desired enantiomer of 1-(2,6-dichloro-3-fluorophenyl)ethanol, than the undesired enantomer, thereby, in one step, resulting in the optically enriched enantiomer.

Suitable in principle for the method according to the invention are all microorganisms such as fungi, yeasts or bacteria or enzymes or enzyme systems such as the various alcohol and aldehyde dehydrogenases, the lactate or formate dehydrogenases, preferably alcohol and aldehyde dehydrogenases, able to reduce carbonyl compounds or aldehydes to the alcohols. The microorganisms can be used directly after cultivation (wet biomass) or after lyophilization (dry matter) for the process according to the invention. The microorganisms or enzymes advantageously used are those able to reduce 1-(2,6-dichloro-3-fluorophenyl)ethanone to the desired enantiomer of 1-(2,6-dichloro-3-fluorophenyl)ethanol with an enantiomeric purity exceeding 85% ee, preferably exceeding 90% ee and very particularly preferably exceeding 95% ee. Examples of suitable microorganisms are organisms of the genera *Alcaligenes, Aspergillus, Beauveria, Candida, Cryptococcus, Curvularia, Diplodia, Endomycopsis, Geotrichum, Hansenula, Kloeckera, Kluyveromyces, Lactobacillus, Mucor, Nocardia, Penicillium, Pfaffia, Pichia, Pseudomonas, Rhodococcus, Rhodotorula, Saccharomyces, Schizosaccharomyces, Sporidiobolus, Streptomyces, Torulopsis* or *Yarrowia*. The following species of the abovementioned genera are advantageously used: *Alcaligenes eutrophus, Aspergillus niger, Aspergillus fumigatus, Beauveria bassiana, Candida guilliennondii, Candida lipolytica, Candida membranaefaciens, Candida methylica, Candida parapsilosis, Candida magnoliae, Candida rugosa, Candida utilis, Curvularia falcata, Diplodia gossypina, Cryptococcus macerans, Geotrichum candidum, Hansenula anomala, Hansenula beckii, Hansenula holstii, wingei, Hansenula polymorpha, Mucor sp., Nocardia rubropertincta, Pfaffia rhodozyma, Pichia glucozyma, Pichia fermentans, Pichia capsulata, Pichia guilliermondii, Pichia membranaefaciens, Pichia pastoris, Pseudomonas fluorescens, Pseudomonas cepacia, Rhodococcus erythropolis, Rhodococcus ruber, Rhodotorula rubra, Rhodotorula gracilis, Rhodotorula glutinis, Rhodotorula minuta, Rhodotorula termusruber, Saccharomyces cerevisiae, Saccharomyces uvarum, Saccharomyces dairensis, Saccharomyces rouxii, Saccharomyces pastorianus, Saccharomyces kluyveri, Schizosaccharomyces japonicus, Schizosaccharomyces malidevorans, Schizosaccharomyces octosporus, Schizosaccharomyces pombe, Torulopsis enokii, Torulopsis methanothermo* and *Yarrowia lipolytica*. The various yeast genera such as *Candida, Hansenula, Kloeckera, Kluyveromyces, Pfaffia, Pichia, Rhodotorula, Saccharomyces, Schizosaccharomyces, Torulopsis* and *Yarrowia* are preferably used. Particularly preferably used are the genera and species *Candida guilliermondii, Candida lipolytica, Candida membranaefaciens, Candida methylica, Candida parapsilosis, Candida magnoliae, Candida rugosa, Candida utilis, Hansenula anomala, Hansenula beckii, Hansenula holstii, wingei, Hansenula polymorpha, Pfaffia rhodozyma, Pichia glucozyma, Pichia fermentans, Pichia capsulata, Pichia guilliermondii, Pichia membranaefaciens, Pichia pastoris, Rhodotorula rubra, Rhodotorula gracilis, Rhodotorula glutinis, Rhodotorula minuta, Rhodotorula termusruber, Saccharomyces cerevisiae, Saccharomyces uvarum, Saccharomyces dairensis, Saccharomyces kluyveri, Saccharomyces rouxii, Saccharomyces pastorianus, Saccharomyces kluyveri, Schizosaccharomyces japonicus, Schizosaccharomyces malidevorans, Schizosaccharomyces octosporus, Schizosaccharomyces pombe, Torulopsis enokii, Torulopsis methanothermo* and *Yarrowia lipolytica*, very particularly preferably the genera and species *Rhodotorula rubra, Saccharomyces cerevisiae, Saccharomyces uvarum, Schizosaccharomyces japonicus, Pichia fermentans, Hansenula polymorpha, Rhodotorula gracilis, Candida utilis* and *Candida magnoliae*.

Microorganisms may be genetically transformed to improve enzyme production in a cell, to provide coenzyme-regenerating enzymes in the same cell, to improve poor enantioselectivities due to presence of plural enzumes in a cell with overlapping substrate specificities but different enantioselectivities, to solve the problem of overmetabolism, etc. as described, for example, in Nakamura et al. *Tetrahedron: Asymmetry*, 2003, vol. 14, pp. 2659-2681.

One or more of any suitable microorganism may be used in the processes of the present invention. As described earlier, the microorganism used in the subject processes may be intact, any suitable preparation thereof, e.g., a broken cell preparation thereof, a dehydrated preparation thereof, and be either free or immobilized. However, where a non-intact microorganism is employed in the present invention such as, for example, a broken cell preparation, e.g., cell extract, acetone powder enzymatic preparation, or the enzyme derived therefrom, those skilled in the art would understand that a suitable co-factor for the enzyme is also included.

Those skilled in the art will understand from the description provided herein and their related knowledge how to prepare a suitable broken cell preparation such as described, for example, in Patel et al., *Appl. Environ. Microbiol.*, 1979, vol. 38, pp. 219-223. Those skilled in the art will understand from the description provided herein and their related knowledge how to prepare a suitable acetone powder enzymatic preparation such as described, for example, in. Nakamura et al., *Tetrahedron Lett.*, 1996, vol. 37, pp. 1629-1632; Nakamura et al., *Tetrahedron: Asymmetry*, 2003, vol. 14, pp. 2659-2681.

The enzyme may be any enzyme obtainable from animals, plants, microorganisms, etc. The enzyme may be employed in any conventional form such as in a purified form, a crude form, a mixture with other enzymes, a microbial fermentation broth, a fermentation broth, a microbial body, a filtrate of fermentation broth, and the like, either solely or in combination. In addition, the enzyme or microbial body may be immobilized on a resin.

In addition, an enzyme (e.g., an oxidoreductase) of any suitable microorganism may also be used in the subject processes, and this enzyme may be isolated from the microorganism by any suitable method known to those skilled in the art and, as for the intact microorganism, may be used in the subject process in either free or immobilized form. Those skilled in the art will understand from the description provided herein and their related knowledge how to isolate and purify the enzyme of the suitable microorganism such as described, for example, in WO 03/093477.

Exemplary, commercially available enzymes suitable for use in the present invention include dehydrogenases and reductases, which are classified under E.C.1.1.1 and capable of catalyzing the reduction of carbonyl groups, such as, for example, a KRED-M27 KIT of ketone reductases from Biocatalytics, Inc., horse liver alcohol dehydrogenase (Grunwald et al., *J. Am. Chem. Soc.*, 1986, vol. 108, pp. 6732-6734; Johansson et al., *Eur. J. Biochem.*, 1995, vol. 227, pp. 551-555; Adolph et al., *Biochemistry*, 2000, vol. 39, pp. 12885-12897; Wong et al. *Terahedron Organic Chemistry*, 1994, vol. 12, pp. 149-150), yeast alcohol dehydrogenase, *Thermoanaerobium brokii* alcohol dehydrogenase and *Lactobacillus kefir* alcohol dehydrogenase.

The natural substrates of the enzymes are alcohols such as ethanol, lactate, glycerol, etc. and the corresponding carbonyl compounds; however, unnatural ketones can also be reduced enantioselectively. To exhibit catalytic activities, the enzymes require a coenzyme such as NADH or NADPH from which a hydride is transferred to the substrate carbonyl carbon. There are four stereochemical patterns that enable the transfer of the hydride from the coenzyme, NAD(P)H, to the substrate. With E1 and E2 enzymes, the hydride attacks the si-face of the carbonyl group, whereas with E3 and E4 enzymes, the hydride attacks the re-face, which results in the formation of (R) and (S)-alcohols, respectively. On the other hand, E1 and E3 enzymes transfer the pro-(R)-hydride of the coenzyme, and E2 and E4 enzymes use the pro-(S)-hydride. Examples of the E1-E3 enzymes are as follows:

E1: *Pseudomonas* sp. alcohol dehydrogenase
*Lactobacillus kefir* alcohol dehydrogenase
E2: *Geotrichum candidum* glycerol dehydrogenase
*Mucor javanicus* dihydroxyacetone reductase
E3: Yeast alcohol dehydrogenase
Horse liver alcohol dehydrogenase
*Moraxella* sp. alcohol dehydrogenase The directed evolution of enzymes may be used to improve the reducing function of the enzymes or biocatalysts for reduction may be tailored by using catalytic antibodies technique as described, for example, in Nakamura et al. *Tetrahedron: Asymmetry*, 2003, vol. 14, pp. 2659-2681.

The microorganisms suitable for use in the subject stereoselective microbial reduction may be prepared by any suitable method known to those skilled in the art. An example of a suitable method for the preparation of a microorganism from a commercially purchased stock is provided below. The method provided below may be used for any microorganism suitable for use in the present inventive process, and those skilled in the art will understand from the description provided herein how to modify any part of the procedure, e.g., method of preparing the microorganism, free or immobilized, washed or unwashed; method of contacting of the amount of the substrate with the microorganism; growth medium components and conditions, e.g., temperature, pH and the like; or incubation conditions, to achieve the desired result in any particular process.

Those skilled in the art will understand from the description provided herein how to prepare suitable immobilized microorganism such as described, for example, in Bauer et al., *Biotechnol. Lett.*, 1996, 18, pp. 343-348 or suitable immobilized enzyme such as described, for example, in Svec, F.; Gemeiner, P. "Engineering aspects of carriers for immobilized biocatalysts." *Biotechnology &Genetic Engineering Reviews* 1996, vol. 13, pp. 217-235.

Any suitable method of contacting the amount of the substrate with the microorganism or enzyme reduction system can be used in the present invention. The substrate can be contacted with the microorganism or the enzyme reduction system in any suitable order. For example, the substrate can be added to a medium, such as a culture broth, comprising the microorganism, free or immobilized, or some combination thereof; or the medium can comprise the substrate and the microorganism can then be added to such medium; or the substrate and the microorganism can be added together to such medium; or the substrate can be added to a broken cell preparation thereof; or the substrate can be added to a dehydrated preparation of the microorganism; or either the substrate or the microorganism or enzyme reduction system can be added to a suitable solvent comprising the other; and the like. For example, the enzyme reduction system can be added to an appreciably organic solvent with the contacting occurring by adding the substrate to that solvent. Those skilled in the art will also understand based on the present description how to contact by adding the substrate adsorbed to a resin. Moreover, those skilled in the art will understand from the description provided herein how to modify any part of the subject process as desired.

For the process according to the invention, the microorganisms can be first cultivated under nitrogen-limited conditions and, after harvesting the cells, for example by centrifugation, used for the process according to the invention. The reduction can be carried out with whole cells, cell digests or crude enzyme extracts obtained from the cells, or purified enzymes. The process can be carried out in aqueous medium in the presence of a carbon source in the case of whole cells or of a reducing agent such as NADH or NADPH and of a cofactor recycling, such as with the aid of formate dehydrogenase and formic acid, and, where appropriate, other enzymes in the case of cell digests, crude extracts or pure enzymes. Addition of further nutrients in the reduction with whole cells, such as a nitrogen source, vitamins or phosphates, is inexpedient because unwanted side reactions are observed under these conditions, for example, which can result in deficient product quality or else workup problems. Suitable as carbon source for the microorganisms are all carbon sources able to provide the cells with the reducing equivalents necessary for the reduction. Examples of carbon sources which may be mentioned here are mono- or disaccharides such as glucose, mannose, maltose, sucrose, primary or secondary alcohols such as methanol, ethanol, propanol, polyols such as glycerol, lower carboxylic acids such as lactic acid, malic acid or amino acids such as glutamate. Conversion of the precursor with microorganisms in aqueous solution in the presence of a carbon source has the advantage that neither precursor nor product is metabolized and no by-products are formed.

The reaction of bio-reduction can be carried out in pure water or in aqueous buffers without addition of other solvents or solvent mixtures. To improve the solubility of the precursor, 1-(2,6-dichloro-3-fluorophenyl)ethanone, it is possible to add water-miscible organic solvents such as terahydrofuran, acetonitrile, dimethylformamide, dimethylsulfoxide, dimethylacetamide, primary or secondary alcohols, carboxylic acids, lactones such as γ-butyrolactone, which are able to improve the solubility of the precursor, 1-(2,6-dichloro-3-fluorophenyl)ethanone, to the reaction.

The reaction may be carried out at from 0° C. to 50° C., preferably from 10° C. to 45° C., particularly preferably from 15° C. to 40° C.

The reaction times depend on microorganism or enzyme and are from 1 to 72 hours, preferably from 1 to 48 hours.

Any suitable duration of growth of the microorganism, contacting of the microorganism with the amount of the substrate, and incubation of the substrate with the microorganism can be used in the present invention. Suitable growth of the microorganism may be achieved, e.g., within about 24 h, 48 h, or 72 h, at which time a suitable aliquot of a solution of the amount of the substrate in a suitable solvent, preferably ethanol, may be added to the culture. The fermentation may then be continued for, e.g., from about two to about six days, and preferably, e.g., for about five days. The progress of the reaction can easily be followed by conventional methods after extraction of the product with an organic solvent. The fermentation broth may be extracted using any suitable extraction method whereby, for example, a suitable solvent, such as, for example, ethylacetate, methyl isobutylketone, methyl ethylketone, methylene chloride, and the like, preferably, ethylacetate, removes the organic components from the fermentation broth. Methanol can also be used to extract material from the cells into the methanol-water mixture. After extraction of the fermentation broth and separation of the organic and aqueous phases, the compounds comprising the organic residue may be determined using any suitable method, such as, for example, chromatography, preferably, chiral HPLC.

The reaction is preferably carried out under aerobic conditions, i.e., with aeration in the case of conversion with microorganisms, preferably with gentle aeration. However, conversion under anaerobic conditions is also possible. The process can be carried out continuously or batchwise.

The product from any of the above reactions may be purified by phase separation and/or extraction into a suitable solvent, such as dichloromethane and thereafter, if required it may be chromatographed.

The above mentioned reactions may also be carried out using continuous production methods involving continuous recycling of the organic phase in the reaction or immobilization of the cells and passing the substrate in organic solution over the immobilized biomass in a column, loop reactor or other similar reactor.

Hence, as would be understood by those of skill in the art, variation of the growth medium, the conditions of fermentation, and/or the conditions of the reduction (e.g., the temperature, pH, and the amount of substrate) can be altered to control the yield of the resultant compounds and their relative rates of production. In general, the techniques employed in the present invention will be chosen with regard to industrial efficiency. The growth media, conditions of fermentation and relative amounts of microorganism, or enzyme reduction system, and of the substrate described herein, are merely illustrative of the wide variety of media, fermentation conditions and amounts of starting materials which may be suitably employed in the present invention as would be appreciated by those skilled in the art, and are not intended to be limiting in any way.

Any suitable methods for isolating and/or purifying any of the products of the subject processes may be used in the present invention including filtration, extraction, crystallization, column chromatography, thin-layer chromatography, preparative low pressure liquid chromatography or HPLC, or any suitable combination of such methods.

The present invention is illustrated by the following EXAMPLES. The foregoing and following description of the present invention and the various embodiments are not intended to be limiting of the invention but rather are illustrative thereof. Hence, it will be understood that the invention is not limited to the specific details of these EXAMPLES.

EXAMPLES

Materials.

Suitable 96 well plates and accessories were obtained from VWR international. Analytical instruments including the Tecan Genesis 2000 Workstation (Research Triangle Park, NC), Agilent 220 HPLC auto sampler and 6890N GC (Agilent Technologies, CA), SpectraMax Plus 384 (Molecular Devices, USA), Beckman Coulter P/ACE MDQ (Fullerton, Calif.), and Waters/Micromass ZQ LC/MS (Waters, Mass.) were purchased from their respective suppliers. Eppendorf thermomixer-R was purchased from VWR. Chiral HPLC columns used in analysis were obtained from Chiral Technologies (Exton, Pa.) and Phenomenex (Torrance, Calif.).

The majority of enzymes utilized in screening plate were obtained from various enzyme suppliers including Amano (Nagoya, Japan), Roche (Basel, Switzerland), Novo Nordisk (Bagsvaerd, Denmark), Altus Biologics Inc. (Cambridge, Mass.), Biocatalytics (Pasadena, Calif.), Toyobo (Osaka, Japan), Sigma and Fluka. Table 1 illustrates specific enzyme sources corresponding to each enzyme. The Lipase-PS Activity kit was purchased from Sigma. Commercially available pig liver esterase was purchased from Biocatalytics (Pasadena, Calif.) as a crude ammonium sulfate suspension sold under the name PLE AS (Catalog # ICR-123).

The majority of solvents utilized during optimization was obtained from EM Science (Gibbstown, N.J.) and were of the highest purity available.

HPLC Methods

HPLC analysis of the screened samples was performed on an Agilent 1100 HPLC with 96 well auto sampler. Reactions were performed in an Eppendorf thermomixer-R (VWR).

Every HPLC sample was made by taking 2×50 µL from the reaction mixture, then combined and diluted with 2 mL of acetonitrile. 100 µL of that solution were further diluted with 400 µL of acetonitrile and injected in the HPLC.

Non-chiral HPLC Method

Using detector wavelength 254 nm; Phenomenex luna C18 column, 3 µm, C18, 4.6×30 mm; flow rate 2.0 mL/min; injection volume: 5 µL; mobile phases: A: Water-0.1% trifluoroacetic acid (TFA) B: Acetonitrile-0.1% TFA; samples were run on the gradient (0.5 min post-run)

|   | Time | % B  | % C | % D |
|---|------|------|-----|-----|
| 1 | 0.00 | 5.0  | 0.0 | 0.0 |
| 2 | 1.67 | 65.0 | 0.0 | 0.0 |
| 3 | 2.00 | 95.0 | 0.0 | 0.0 |
| 4 | 2.50 | 95.0 | 0.0 | 0.0 |
| 5 | 2.60 | 5.0  | 0.0 | 0.0 |
| 6 | 3.00 | 5.0  | 0.0 | 5.0 |

Chiral HPLC Methods

Alcohol 1: using detector wavelength: 254 nm; Chiralcel ADR-H, 3 µm, C18, 4.6×150 mm; flow rate 0.8 mL/min; injection volume: 10 µL; mobile phases: A: Water B: Acetonitrile; isocratic: 50% B for 15 min.

Acetate 2: chiral method using detector wavelength: 254 nm; Chiralcel OJ-RH, 3 µm, C18, 4.6×150 mm; flow rate 0.6 mL/min; injection volume: 10 µL; mobile phases: A: Water B: Acetonitrile; isocratic: 50% B for 15 min.

Preparation of Screening Plates

Preparation of screening plates has been carried out in according to Yazbeck et al., *Adv. Synth. Catal.*, 2003, vol. 345, pp. 524-532.

Specifically, preparation usually takes on the order of 1-2 days and entails the preparation of the enzyme stock solutions (100 mg/mL) and the dispensing of these stock solutions into 96-well screening plates, or "screening kits". The dispensing of the stock solutions into a screening plate is carried out by an automated liquid handler workstation, which can be programmed to accurately dispense 10 µL of each individual enzyme into the appropriate location in each 96-well plate.

When choosing a 96-well plate format, the plates need to be both solvent and temperature resistant, therefore, it is recommended to use polypropylene plates. The plate volume and morphology also need to be considered. The reactions herein are carried out in 100 µL reaction volumes in plates no larger than 500 µL. V-bottom plates tend to improve solution agitation and allow for cleaner sampling after centrifugation.

Once the plates are prepared, they can be sealed with either adhesive foil or with a penetrable mat cover and stored at −80° C. for months or even years.

In cases where anhydrous conditions are required, such as acylation and amidation reactions, the screening plates must be lyophilized prior to use. In order to remove the water from each well, the plate is lyophilized for 10 to 24 hours at a chamber temperature of −20° C. After lyophilization, the plates can be stored at 4 to 8° C.

Procedure for Enzyme Screening

The resolution of 1-(2,6-dichloro-3-fluorophenyl)ethyl acetate was carried out as follows. A 96-well plate prepared as described above was thawed for 5 minutes. 80 µL of potassium phosphate buffer (0.1 M, pH 7.2) was then dispensed into the wells using a multi-channel pipette. 10 µL of the substrate stock solution (50 mg/mL acetonitrile) was then added to each well via a multi-channel pipette, and the 96 reactions were incubated at 30° C. and 750 rpm. The reactions were sampled after 16 hours by the transfer of 25 µL of the reaction mixture into a new 96-well plate, which was then quenched by the addition of 150 µL of acetonitrile. The 96-well plate was then centrifuged, and the organic supernatant transferred from each well into another 96-well plate. Sampled reactions were then sealed using a penetrable mat cover and transferred to an HPLC system for analysis. The same plate was used to analyze the samples for both reactivity and enantioselectivity using alternating columns on the HPLC simultaneously.

Example 1

Preparation of Optically Active 1-(2,6-dichloro-3-fluorophenyl)ethanol by Combination of Enzymatic Resolution and Chemical Transformation For illustrative purposes only, the process of the present invention is demonstrated by the following example of biotransformation of a racemic 1-(2,6-dichloro-3-fluorophenyl)ethyl acetate, which biotransformation is represented by Scheme 1.

Scheme 1

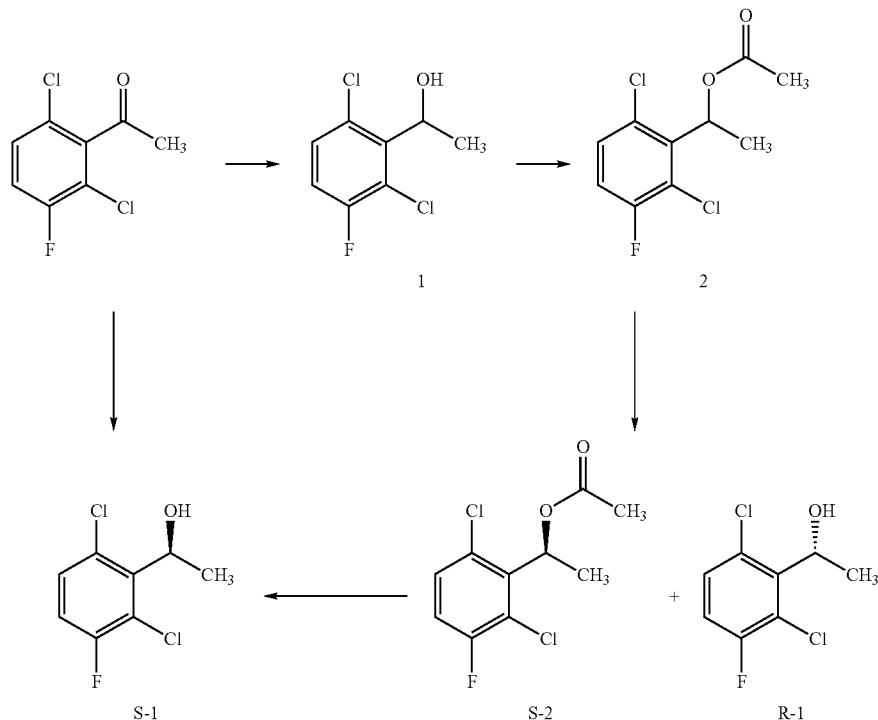

Enzymatic resolution of 1-(2,6-dichloro-3-fluorophenyl) ethyl acetate (2)

The process involved performing four main steps:

1) preparing racemic 1-(2,6-dichloro-3-fluorophenyl)ethyl acetate 2) enzyme screening using commercially available lipases, proteases and esterases;

3) optimizing the reaction conditions such as pH, temperature and the amount of enzyme and substrate; and 4) maximizing yield of the enzymatic resolution method by developing a procedure for combination of enzymatic hydrolysis, esterification and chemical hydrolysis with inversion.

1) Preparing Racemic 1-(2,6-Dichloro-3-Fluorophenyl) Ethyl Acetate (Compound 2)

Compound 1

1-(2,6-dichloro-3-fluorophenyl)ethanol

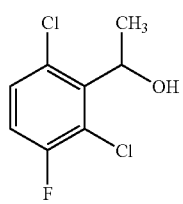

Sodium borohydride (90 mg, 2.4 mmol) was added to a solution of 2',6'-dichloro-3'-fluoro-acetophenone (Aldrich, catalog # 52,294-5) (207 mg, 1 mmol) in 2 mL of anhydrous $CH_3OH$. The reaction mixture was stirred at room temperature for 1 h then was evaporated to give a colorless oil residue. The residue was purified by flash chromatography (eluting with 0→10% EtOAc in hexanes) to give compound 1 as a colorless oil (180 mg; 0.88 mmol; 86.5% yield); MS (APCI) (M−H)⁻ 208; 1H NMR (400 MHz, chloroform-D) δ ppm 1.64 (d, J=6.82 Hz, 3H) 3.02 (d, J=9.85 Hz, 1H) 6.97-7.07 (m, 1H) 7.19-7.33 (m, 1H).

Compound 2

1-(2,6-dichloro-3-fluorophenyl)ethyl acetate

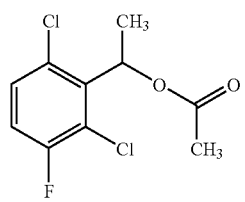

Acetic anhydride (1.42 mL, 15 mmol) and pyridine (1.7 mL, 21 mmol) were added sequentially to a solution of compound 1 (2.2 g, 10.5 mmol) in 20 mL of $CH_2CL_2$. The reaction mixture was stirred at room temperature for 12 h and then evaporated to give a yellowish oil residue. The residue was purified by flash chromatography (eluting with 7→9% EtOAc in hexanes) to give compound 2 as a colorless oil (2.26 g; 9.0 mmol; 85.6% yield); 1H NMR (400 MHz, chloroform-D) δ ppm 1.88 (d, J=6.82 Hz, 3H) 2.31 (s, 3H) 6.62 (q, J=6.82 Hz, 1H) 7.25 (t, J=8.46 Hz, 1H) 7.49 (dd, J=8.84, 5.05 Hz, 1H)

2) Enzyme Screening

The most suitable catalyst for the kinetic resolution of racemic 1-(2,6-dichloro-3-fluorophenyl)ethyl acetate (compound 2) was identified after screening a collection of commercially available hydrolases. A general enzyme screening method was used to screen 94 commercially available enzymes represented in Table 1.

TABLE 1

Biotranformations Group Enzyme Screening Kit (G3)

|   | 2 | 3 | 4 | 5 | 6 | 7 | 8 | 9 | 10 | 11 | 12 |
|---|---|---|---|---|---|---|---|---|---|---|---|
| A | Blank | PGRD9 | PGRD17 | PGRD25 | PGRD33 | PGRD41 | PGRD49 | PGRD57 | PGRD65 | PGRD73 | PGRD81 | PGRD89 |
| B | Blank | PGRD10 | PGRD18 | PGRD26 | PGRD34 | PGRD42 | PGRD50 | PGRD58 | PGRD66 | PGRD74 | PGRD82 | PGRD90 |
| C | PGRD3 | PGRD11 | PGRD19 | PGRD27 | PGRD35 | PGRD43 | PGRD51 | PGRD59 | PGRD67 | PGRD75 | PGRD83 | PGRD91 |
| D | PGRD4 | PGRD12 | PGRD20 | PGRD28 | PGRD36 | PGRD44 | PGRD52 | PGRD60 | PGRD68 | PGRD76 | PGRD84 | PGRD92 |
| E | PGRD5 | PGRD13 | PGRD21 | PGRD29 | PGRD37 | PGRD45 | PGRD53 | PGRD61 | PGRD69 | PGRD77 | PGRD85 | PGRD93 |
| F | PGRD6 | PGRD14 | PGRD22 | PGRD30 | PGRD38 | PGRD46 | PGRD54 | PGRD62 | PGRD70 | PGRD78 | PGRD86 | PGRD94 |
| G | PGRD7 | PGRD15 | PGRD23 | PGRD31 | PGRD39 | PGRD47 | PGRD55 | PGRD63 | PGRD71 | PGRD79 | PGRD87 | PGRD95 |
| H | PGRD8 | PGRD16 | PGRD24 | PGRD32 | PGRD40 | PGRD48 | PGRD56 | PGRD64 | PGRD72 | PGRD80 | PGRD88 | PGRD96 |

Lipases
Proteases

| PGRD # | Enzyme | Supplier Code |
|---|---|---|
| 1 | Blank [Buffer] | Blank |
| 2 | Blank [ACN] | Blank |
| 3 | Porcine Pancreatic Lipase | Altus03 |
| 4 | CALA, lyo. | Altus11 |
| 5 | *Candida lipolytica* Lipase | Altus12 |
| 6 | CALB, lyo. | Altus13 |
| 7 | *Geotrichum candidum* Lipase | Altus28 |
| 8 | *Pseudomonas aroginosa* Lipase | Altus50 |
| 9 | *Aspergillus niger* Lipase | Amano Lipase A |
| 10 | *Pseudomonas cepacia* Lipase | Amano Lipase AH |
| 11 | *Pseudomo.fluorescens* Lipase | Amano Lipase AK |
| 12 | *Candida rugosa* Lipase | Amano Lipase AY |
| 13 | *Rhizopus delemar* Lipase | Amano Lipase D |
| 14 | *Rhizopus oryzae* Lipase | Amano Lipase F |
| 15 | *Penicillium camembertii* Lipase | Amano Lipase G |
| 16 | *Mucor javanicus* Lipase | Amano Lipase M |
| 17 | *Pseudomonas cepacia* Lipase | Amano Lipase PS |
| 18 | *Penicillium roqueforti* Lipase | Amano Lipase R |
| 19 | *Aspergillus* sp. Protease | BioCatalytics101 |
| 20 | *Pseudomonas* sp. Lipase | BioCatalytics103 |
| 21 | Fungal Lipase | BioCatalytics105 |
| 22 | Micorbial, lyo. Lipase | BioCatalytics108 |
| 23 | CALB, lyo. | BioCatalytics110 |
| 24 | *Candida* sp., lyo | BioCatalytics111 |
| 25 | CALA, lyo. | BioCatalytics112 |
| 26 | *Thermomyces* sp Lipase | BioCatalytics115 |
| 27 | *Alcaligines* sp., lyo. Lipase | BioCatalytics117 |
| 28 | *Chromobacterium viscosum* Lipase | Altus 26 |
| 29 | CalB, L2 Sol | Chriazyme L2 Sol |
| 30 | *Candida utilis* Lipase | Fluka6 |
| 31 | *Rhizopus niveus* Lipase | Sigma L8 |
| 32 | *Pseudomonas* species Lipoprotein Lipase | Sigma L13 |
| 33 | *Thermomuces lanuginosus* Lipase | Sigma L9 Lipolase |
| 34 | *Thermomuces lanuginosus* Lipase | Sigma L10 Novo871 |
| 35 | *Rhizomucor miehei* Lipase | Sigma L6 Palatase |
| 36 | *Pseudomonas* species Lipase | Sigma L14 Type XIII |
| 37 | Wheat Germ Lipase | Sigma L11 |
| 38 | *Rhizopus arrhizus* Lipase | Sigma L7 Type XI |
| 39 | Pancreatic Lipase 250 | Valley Research V1 |
| 40 | Trypsin Protease | Altus33 |
| 41 | *Chymopapain* Protease | Altus38 |
| 42 | *Bromelain* Protease | Altus40 |
| 43 | *Aspergillus niger* Protease | Altus41 |
| 44 | *Aspergillus oryzae* Protease | Altus42 |
| 45 | *Penicillium species* Protease | Altus43 |
| 46 | *Aspergillus* sp. Protease | Altus45 |
| 47 | Renin Calf Stomach protease | Sigma P24 |
| 48 | *Subtilisin Carlsberg* | Altus10 |
| 49 | *Bacillus lentus* Protease | Altus53 |

TABLE 1-continued

Biotranformations Group Enzyme Screening Kit (G3)

|   | 1 | 2 | 3 | 4 | 5 | 6 | 7 | 8 | 9 | 10 | 11 | 12 |
|---|---|---|---|---|---|---|---|---|---|---|---|---|
| A | Blank | PGRD9 | PGRD17 | PGRD25 | PGRD33 | PGRD41 | PGRD49 | PGRD57 | PGRD65 | PGRD73 | PGRD81 | PGRD89 |
| B | Blank | PGRD10 | PGRD18 | PGRD26 | PGRD34 | PGRD42 | PGRD50 | PGRD58 | PGRD66 | PGRD74 | PGRD82 | PGRD90 |
| C | PGRD3 | PGRD11 | PGRD19 | PGRD27 | PGRD35 | PGRD43 | PGRD51 | PGRD59 | PGRD67 | PGRD75 | PGRD83 | PGRD91 |
| D | PGRD4 | PGRD12 | PGRD20 | PGRD28 | PGRD36 | PGRD44 | PGRD52 | PGRD60 | PGRD68 | PGRD76 | PGRD84 | PGRD92 |
| E | PGRD5 | PGRD13 | PGRD21 | PGRD29 | PGRD37 | PGRD45 | PGRD53 | PGRD61 | PGRD69 | PGRD77 | PGRD85 | PGRD93 |
| F | PGRD6 | PGRD14 | PGRD22 | PGRD30 | PGRD38 | PGRD46 | PGRD54 | PGRD62 | PGRD70 | PGRD78 | PGRD86 | PGRD94 |
| G | PGRD7 | PGRD15 | PGRD23 | PGRD31 | PGRD39 | PGRD47 | PGRD55 | PGRD63 | PGRD71 | PGRD79 | PGRD87 | PGRD95 |
| H | PGRD8 | PGRD16 | PGRD24 | PGRD32 | PGRD40 | PGRD48 | PGRD56 | PGRD64 | PGRD72 | PGRD80 | PGRD88 | PGRD96 |

Lipases

Proteases

| PGRD # | Enzyme | Supplier Code |
|---|---|---|
| 50 | *Aspergillus niger* Protease | Amano Acid Protease A |
| 51 | *Rhizopus niveus* Protease | Amano Acid Protease II |
| 52 | *Rhizopus niveus* Protease | Amano Newlase F |
| 53 | *Rhizopus oryzae* Protease | Amano Peptidase R |
| 54 | *Bacillus subtilis* Protease | Amano Proleather FGF |
| 55 | *Aspergillus oryzae* Protease | Amano Protease A |
| 56 | *Aspergillus oryzae* Protease | Amano Protease M |
| 57 | *Bacillus subtilis* Protease | Amano Protease N |
| 58 | *Aspergillus melleus* | Amano Protease P |
| 59 | *Bacillus stearothermophilus* Protease | Amano Protease SG |
| 60 | Pig Liver Esterase, lyo | BioCat Chirazyme E1 |
| 61 | Pig Liver Esterase, lyo | BioCat Chirazyme E2 |
| 62 | *Streptomyces* sp. Proteases | BioCatalytics118 |
| 63 | *Tritirachium album* Protease | Fluka P6 Proteinase K |
| 64 | Bovine Pancreas Protease | Sigma P18 alphachymotrypsin I |
| 65 | *Streptomyces griseus* Protease | Sigma P16 Bacterial |
| 66 | Bovine Pancreas Protease | Sigma P21 Betachymotrypsin |
| 67 | *Clostridium histolyticum* Protease | Sigma P13 Clostripain |
| 68 | Bovine Intestine Protease | Sigma P17 Enteropeptidase |
| 69 | Porcine Intestine Protease | Sigma P25 Enteropeptidase |
| 70 | *Bacillus* species Protease | Sigma P8 Esperase |
| 71 | *Apergillus oryzae* Protease | Sigma P1 Flavourzyme |
| 72 | *Bacillus amyloliquefaciens* Protease | Sigma P5 Neutrase |
| 73 | *Carica papaya* Protease | Sigma P12 Papain |
| 74 | *Bacillus thermoproteolyticus rokko* | Sigma P10 Protease |
| 75 | *Pyrococcus furiosis* Protease | Sigma P14 Protease S |
| 76 | *Bacillus* species Protease | Sigma P9 Savinase |
| 77 | Bovine Pancreas Protease | Sigma P19 Type 1 (crude) |
| 78 | *Bacillus polymyxa* Protease | Sigma P7 Type IX |
| 79 | *Bacillus licheniformis* Protease | Sigma P6 Type VIII |
| 80 | *Aspergillus saitoi* Protease | Sigma P3 Type XIII |
| 81 | *Aspergillus sojae* Protease | Sigma P4 Type XIX |
| 82 | *Aspergillus oryzae* Protease | Sigma P2 Type XXIII |
| 83 | Bacterial Protease | Sigma P11 Type XXIV |
| 84 | *Rhizopus species* newlase | Sigma15 Newlase |
| 85 | *Validase* FP Conc. | Valley15 |
| 86 | *Bromelian* Conc | Valley10 |
| 87 | Acylase from *Aspergillus* Sp. | Amano Am1 |
| 88 | Porcine kidney Acylase | Sigma A-S2 Acylase I |
| 89 | *Penicilin* G Acylase | Altus06 |
| 90 | Esterase from *Mucor Meihei* | Fluka |
| 91 | *Candida rugosa* Esterase | Altus31 |
| 92 | Porcine Pancreatic Elastase | Altus35 |
| 93 | Cholesterol Esterase | BioCatalytics |
| 94 | PLE-Ammon. Sulfate | BioCatalytics 123 |
| 95 | Rabbit Liver Esterase | Sigma ES2 |
| 96 | Cholesterol Esterase *Peudomonas* flu. | Sigma ES4 |

After initial screening using 5% substrate load in 100 mM potassium phosphate buffer at pH 7.2, several hydrolases were identified as hits for the enzymatic hydrolysis of the racemic alcohol ester 2 to alcohol R-1 (Scheme 2).

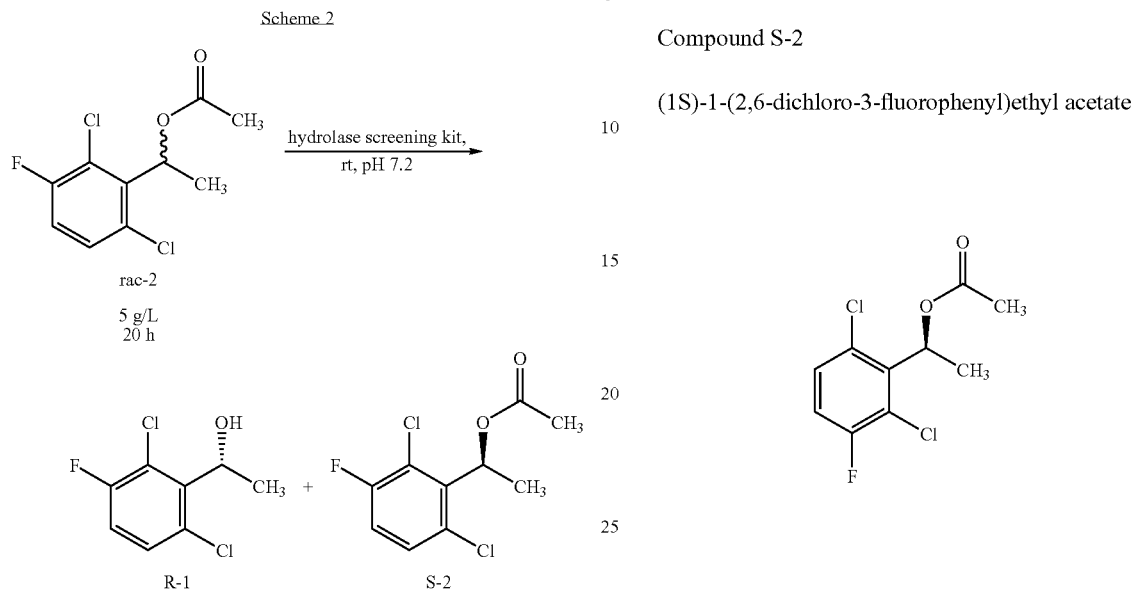

Compound R-1
(1R)-1-(2,6-dichloro-3-fluorophenyl)ethanol

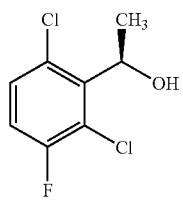

Compound R-1 was purified from compound S-2 by flash chromatography (eluting with 15→17% EtOAc in hexanes) to give compound R-1 as a colorless oil (92.7 mg; 0.45 mmol).

Compound S-2

(1S)-1-(2,6-dichloro-3-fluorophenyl)ethyl acetate

Compound S-2 was purified from compound R-1 by flash chromatography (eluting with 9→10% EtOAc in hexanes) to give compound S-2 as a colorless oil (185.9 mg; 0.74 mmol).

As shown in Table 2, several enzymes showed activity towards 1-(2,6-dichloro-3-fluorophenyl)ethyl acetate (2). The analysis of E values revealed that five of those enzymes showed good enantioselectivity of E value greater than 100. Both lipase from *Rhizopus delemar* and pig liver esterase (PLE) displayed E values >150. However, PLE showed the highest reactivity towards (R)-1-(2,6-dichloro-3-fluorophenyl)ethyl acetate ((R)-2).

TABLE 2

| Enzymes | E value | Reactivity |
|---|---|---|
| Selective for hydrolysis of (R)-acetate | | |
| *Candida Antarctica* lipase B (CAL-B), pig liver esterase (PLE), *Rhizopus delemar* lipase, Porcine Kidney acylase, cholesterol esterase | High (>100) | High |
| Bovine intestinal protease, Sigma protease P6 type VIII, *Candida rugosa* lipase | | Low |
| *Rhizopus orizae* lipase, *Penicillum camembertii* lipase, *Pseudomonas* sp. Lipase, *Thermomyces* sp. Lipase, *Alcaligenes* sp. Lipase, *Chromobacterium viscosum* lipase, *Rhizomucor miehei* lipase, *Thermomyces lanuginosus* lipase, wheat germ lipase, Bromelain protease, *Aspergillus niger* protease, *Rhizopus niveus* protease, *Aspergillus saitoi* protease, acylase from *Aspergillus* sp. | Low (<20) | Low |
| Selective for hydrolysis of (S)-acetate | | |
| *Candida Antarctica* lipase A (CAL-A), Subtilisin Carlsberg (protease from *Bacillus licheniformis*), *Rhizopus orizae* protease | Low (<10) | Low |
| *Rhizopus delemar* lipase | | High |

The absolute configuration of alcohol (1) generated from the PLE hydrolysis was initially assigned by comparison with a known reaction of a similar substrate as shown at Scheme 3 and described in Bouzemi, N. et al, *Tetrahedron Letters*, 2004, pp. 627-630.

Scheme 3

Literature report

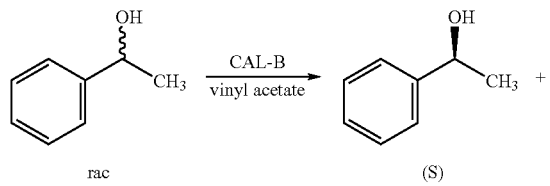

Tested in the lab and assigned (assuming the enzyme does not change the recognition pattern)

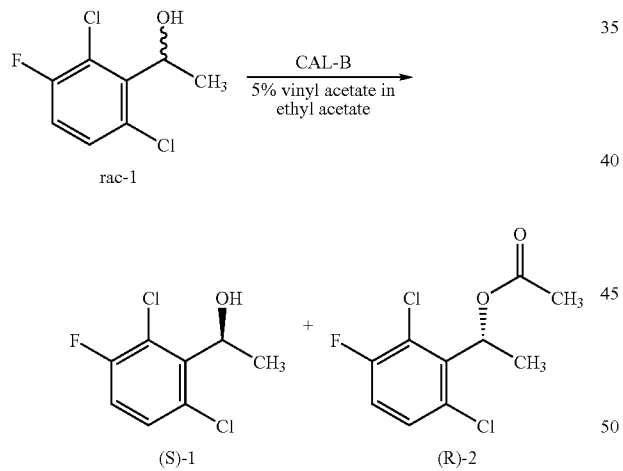

As shown at Scheme 3, the enzymatic acylation of 1-phenylethanol using CAL-B produced the R-enantiomer of 1-phenylethyl acetate leaving the unreacted S-enantiomer of 1-phenylethanol (Bouzemi, N. et al, *Tetrahedron Letters*, 2004, pp. 627-630). One can assume that when CAL-B is reacted with rac-1, the substrate recognition should be the same; accordingly, the obtained ester product was assigned as R-enantiomer.

When compared with the compound obtained in the enzymatic hydrolysis of rac-1 with PLE (opposite reaction), the R isomer of the alcohol was observed, clearly coming from the hydrolysis of the R-acetate.

A direct determination of the absolute configuration of alcohol (1) generated from the PLE hydrolysis product can be based on the NMR determination of the diastereomer produced from the Mosher's esters.

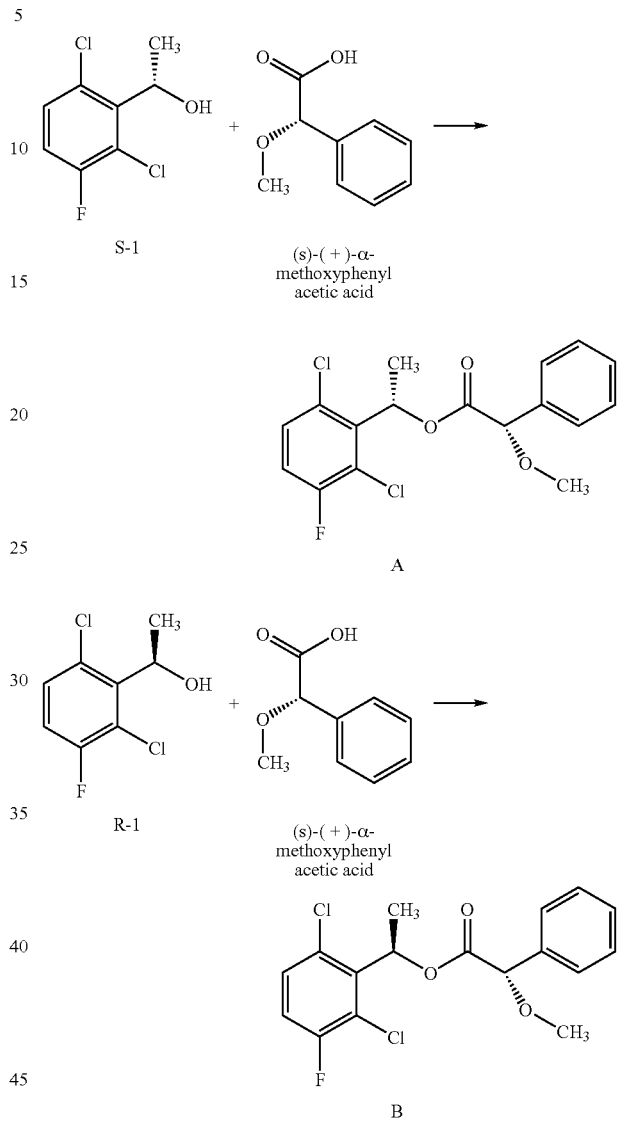

Compound A and compound B were synthesized using literature reported procedures in *Tetrahedron: Asymmetry* 2002, vol. 13, p. 2283; *Tetrahedron Lett.* 1988, vol. 29, p. 6211. These two compounds are subjected for $^1$H-NMR experiments and the chemical shifts of the methyl groups of both compound A and compound B are compared to determine that compound A has the "S" configuration and compound "B" has the "R" configuration.

Synthesis of compound A: DCC(N,N'-dicyclohexylcarbodiimide) (1.1 mmol) was added to a solution of (s)-(+)-a-methoxyphenylacetic acid (1 mmol) in 5 mL of anhydrous THF. The reaction mixture was stirred for 15 min at room temperature under nitrogen atmosphere. Compound S-1 (1 mmol) and DMAP (4-dimethylaminopyridine) (0.2 mmol) were added sequentially to the reaction mixture and the resulting mixture was stirred at room temperature for 36 h. The mixture was evaporated, triturated in methanol, filtered, and concentrated to get a residue. The residue was purified by HPLC to give compound A.

Synthesis of compound B: DCC(N,N'-dicyclohexylcarbodiimide) (1.1 mmol) was added to a solution of (s)-(+)-a-methoxyphenylacetic acid (1 mmol) in 5 mL of anhydrous THF. The reaction mixture was stirred for 15 min at room temperature under nitrogen atmosphere. Compound R-1 (1 mmol) and DMAP (4-dimethylaminopyridine) (0.2 mmol) were added sequentially to the reaction mixture and the resulting mixture was stirred at room temperature for 36 h. The mixture was evaporated, triturated in methanol, filtered, and concentrated to get a residue. The residue was purified by HPLC to give compound B.

3) Optimizing the Reaction Conditions Using PLE-AS

PLE is an enzyme produced by Roche and sold through Biocatalytics Inc. as a crude esterase preparation from pig liver, commonly known as PLE-AS (purchased from Biocatalytics as ICR-123, sold as an ammonium sulfate suspension). The enzyme is classified in the CAS registry as a "carboxylic-ester hydrolase, CAS no. 9016-18-6". The corresponding enzyme classification number is EC 3.1.1.1. The enzyme is known to have broad substrate specificity towards the hydrolysis of a wide range of esters. The lipase activity is determined using a method based on hydrolysis of ethylbutyrate in a pH titrator. 1 LU (lipase unit) is the amount of enzyme which liberates 1 μmol titratable butyric acid per minute at 22° C., pH 8.2. The preparation reported herein (PLE-AS, as a suspension) is usually shipped as an opaque brown-green liquid with a declared activity of >45 LU/mg (protein content around 40 mg/mL).

The main parameters optimized in this reaction were substrate and enzyme concentrations, pH, and type of buffer. Most of the experiments were performed using the liquid form of the enzyme commercially available as PLE-AS. The effect of the pH on this reaction was not very critical. A reasonable range of pH to perform the reaction includes pH 6-9 with optimal results at pH 8.0. Most optimization experiments were then performed at room temperature. Buffers were tested: Tris, phosphate and calcium acetate. The reaction can be performed in the three buffers with very similar results in the range of 10-100 mM concentrations. Other buffers that can be used to carry out the reaction include 2-(N-morpholino)ethanesulfonic acid (MES), piperazine-N,N'-bis(2-ethanesulfonic acid) (PIPES), N,N-bis(2-hydroxyethyl)-2-aminoethanesulfonic acid (BES), 3-(N-morpholino) propanesulfonic acid (MOPS), N-(2-hydroxyethyl) piperazyne-N'-(2-ethanesulfonic acid) (HEPES), N-tris (hydroxymethyl)methyl-2-aminoethanesulfonic acid (TES), tris(hydroxymethyl)aminomethane (TRIZMA), N-tris(hydroxymethyl)methylglycine (TRICINE), N,N-bis(2-hydroxyethyl)glycine (BICINE), N-tris(hydroxymethyl)methyl-3-aminopropanesulfonic acid (TAPS), or any other buffer with pKa values between 6 and 9. Normal stir rates were used in all experiments (500-1000 rpm). It was found that 5-10% (v/v) enzyme content could efficiently catalyze the enzymatic reaction nearly as efficient as 20%. Pre-mixing of enzyme and buffer followed by addition of substrate and strong stirring was found to be beneficial to perform the reaction at minimum concentrations. Using those optimized conditions for enzyme loads, substrate loads from 0.2-2 M were tested and 1-2 M concentrations were found to afford close to 50% conversion within 24 h. Other forms of the enzyme not commercially available could also be used, those include immobilized on solid support (such as ceramic, celite, Eupergit, acrylic beads, etc), cross-linked enzyme crystals (CLECs), or cross-linked enzyme aggregates (CLEAs), ammonium sulfate pellets, or any other form in which activity and enantioselectivity can be preserved or enhanced.

Large-scale preparation of compounds R-1 and S-2 using pig liver esterase resolution of racemic 1-(2,6-dichloro-3-fluorophenyl)ethyl acetate (2) was performed according to Scheme 4.

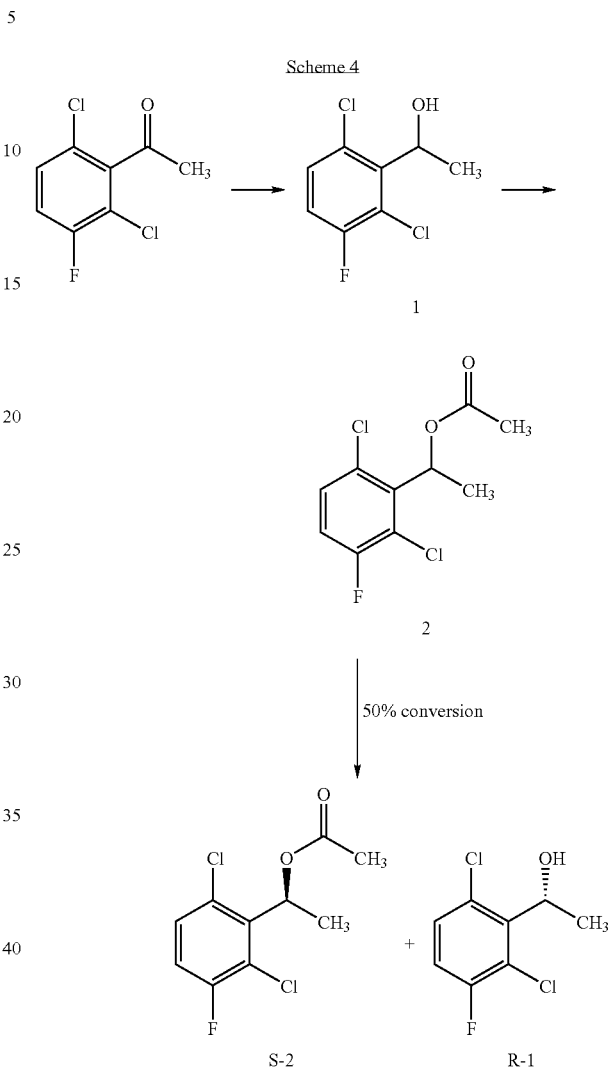

Scheme 4

To a 5 L Reactor equipped with a pH electrode, an overhead stirrer and a base addition line was added the PLE-AS solution (0.125 L) and 2.17 L of potassium phosphate buffer solution. A 718 Stat Titrino-Metrohm pH titrator (Brinkman instruments, Inc) was used to perform the reaction. The potassium phosphate buffer solution was prepared by mixing 2.17 L of water, 15.6 mL of 1M $K_2HPO_4$ solution and 6.2 mL of $KH_2PO_4$.

Then, racemic 1-(2,6-dichloro-3-fluorophenyl)ethyl acetate (2) (250 g, 1 mol) was added. The suspension was then stirred at room temperature for 22 h. The pH of the solution was maintained at 7.0 by adding 2N NaOH. Reaction was followed by RP-HPLC looking at both conversion and % ee of the product, and stopped after 51-52% starting material had been consumed (~240 mL of base added).

After reaction completion, methyl-tertbutyl ether (MTBE) (900 mL) was added, and the mixture stirred for 5 min. The resulting emulsion was passed through a celite filter pad and then transferred to a separatory funnel/extractor. This stage includes slurring celite with deionized water and then pouring in a Buchner funnel prepared the celite pad. Water filtrate was discarded before passing the enzyme emulsion. After the layers were separated, the aqueous layer was extracted two more times with 900 mL of MTBE each. The combined MTBE layers were dried with Na₂SO₄ and concentrated under vacuum to afford 242 g of crude alcohol and acetate mixture.

4) Maximizing Yield of the Enzymatic Resolution Method by Developing a Procedure for Combination of Enzymatic Hydrolysis, Esterification and Chemical Hydrolysis with Inversion Once the enzymatic kinetic resolution was developed, chemical conversion of the "R-1" alcohol to the "S-2" acetate was explored. The process was performed according to Scheme 5.

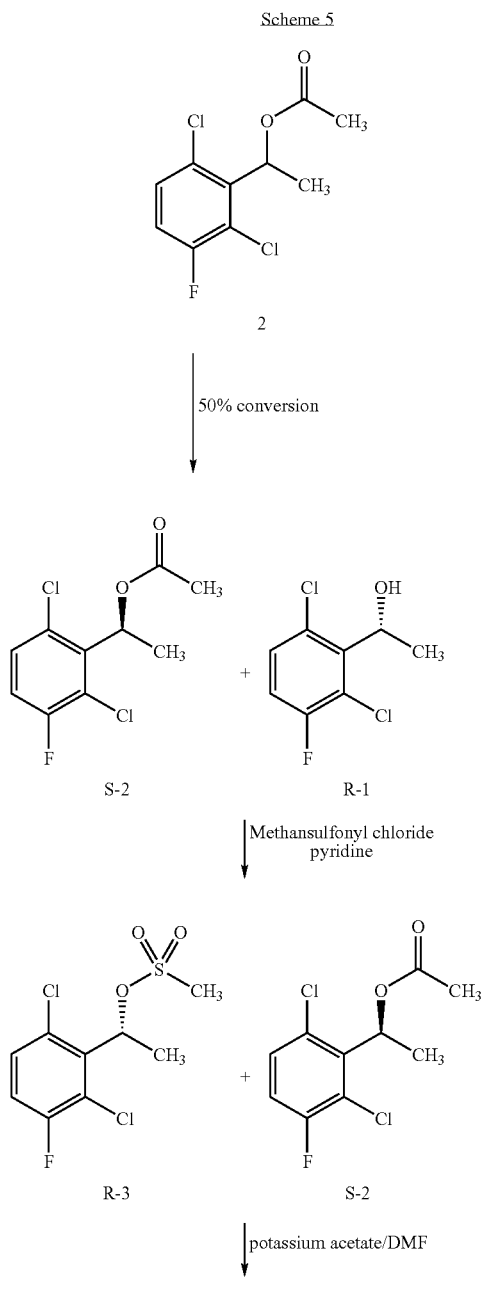

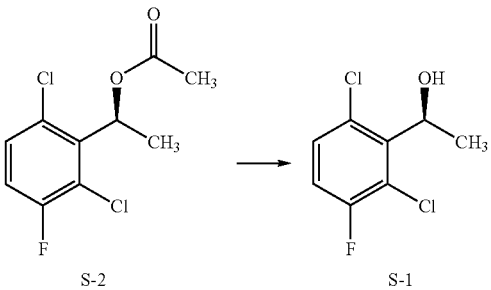

To a 50 mL jacketed flask equipped with a pH electrode, an overhead stirrer and a base addition line (1M NaOH), was added 1.2 ml of 100 mM potassium phosphate buffer pH 7.0 and 0.13 ml of PLE AS suspension. Then, compound 2 (0.13 g, 0.5 mmol, 1.00 eq) was added dropwise and the resulting mixture was stirred at room temperature for 20 h; maintaining the pH of the reaction constant at 7.0 using 1 M NaOH. Both the conversion and ee's of the reaction was monitored by RP-HPLC, and stopped after 50% starting material was consumed (approximately 17 hours under these conditions). The mixture was then extracted three times with 10 mL of ethyl acetate to recover both ester and alcohol as a mixture of R-1 and S-2.

Methanesulfonyl chloride (0.06 mL, 0.6 mmol) was added to a solution of a mixture of R-1 and S-2 (0.48 mmol) in 4 mL of pyridine under nitrogen atmosphere. The reaction mixture was stirred at room temperature for 3 h then evaporated to obtain an oil. Water (20 mL) was added to the mixture and then EtOAc (20 mL×2) was added to extract the aqueous solution. The organic layers were combined, dried, filtered, and evaporated to give a mixture of R-3 and S-2. This mixture was used in the next step reaction without further purification. ¹H NMR (400 MHz, chloroform-D) δ ppm 1.66 (d, J=7.1 Hz, 3H) 1.84 (d, J=7.1 Hz, 3H) 2.09 (s, 3H) 2.92 (s, 3H) 6.39 (q, J=7.0 Hz, 1H) 6.46 (q, J=6.8 Hz, 1H) 6.98-7.07 (m, 1H) 7.07-7.17 (m, 1H) 7.23-7.30 (m, 1H) 7.34 (dd, J=8.8, 4.80 Hz, 1H).

Potassium acetate (0.027 g, 0.26 mmol) was added to a solution of a solution of a mixture of R-3 and S-2 (0.48 mmol) in 4 mL of DMF under nitrogen atmosphere. The reaction mixture was heated to 100° C. for 12 h. Water (20 mL) was added to the reaction mixture and EtOAc (20 mL×2) was added to extract the aqueous solution. The combined organic layer was dried, filtered, and evaporated to give an oil of S-2 (72 mg, 61% yield in two steps). Chirality ee: 97.6%. ¹H NMR (400 MHz, chloroform-D) δ ppm 1.66 (d, J=7.1 Hz, 3H) 2.09 (s, 3H) 6.39 (q, J=6.8 Hz, 1H) 7.02 (t, J=8.5 Hz, 1H) 7.22-7.30 (m, 1H).

Sodium methoxide (19 mmol; 0.5 M in methanol) was added slowly to compound S-2 (4.64 g, 18.8 mmol) under a nitrogen atmosphere at 0° C. The resulting mixture was stirred at room temperature for 4 hr. The solvent was evaporated and H₂O (100 mL) was added. The cooled reaction mixture was neutralized with sodium acetate-acetic acid buffer solution to pH 7. Ethyl acetate (100 mL×2) was added to extract the aqueous solution. The combined organic layers was dried over Na₂SO₄, filtered, and evaporated to obtain S-1 a white solid (4.36 g, 94.9% yield); SFC-MS: 97% ee. ¹H NMR (400 MHz, chloroform-D) δ ppm 1.65 (d, J=6.8 Hz, 3H) 5.58 (q, J=6.9 Hz, 1H) 6.96-7.10 (m, 1H) 7.22-7.36 (m, 1H).

Example 2

Enantioselective Bio-Reduction of 1-(2,6-dichloro-3-fluorophenyl)ethanone

The current process development was approached using whole cell catalyzed reactions as well as commercially available enzymes. The procedure involved performing three main steps:

1) screening of an internal whole cell (or isolated enzyme) collection containing mostly yeast and fungal strains (commercially available alcohol dehydrogenases and ketone reductases);
2) performing reaction optimization on pH, temperature and the amount of enzyme and substrate;
3) developing a procedure for the recycling of biocatalyst.

Whole Cell Screening

The screening for strains capable of doing the enantioselective reduction of 1-(2,6-dichloro-3-fluorophenyl)ethanone was carried out as follows. Microbial strains were grown from frozen stocks in a 96-well plate (5 µL/well). 200 µL of sterile YM media (Difco media 271120) was inoculated in each well. All strains were grown at 28° C. and 250 rpm on a rotary shaker. After 2 days, substrate was added from a 10% stock solution in ethanol to reach 1 mg/mL in each well. The plates were then shaken at the same speed and temperature and the reactions analyzed after 2-7 days. The reactions were analyzed by HPLC using a non-chiral column.

One hundred eighty eight different microbial strains shown in Table 3 were distributed into 96-well plates and tested at substrate concentrations no greater than 1 mg/mL as described above. Thirty different strains belonging to *Rhodotorula*, *Neurospora*, *Rhodosporibium*, *Aerobasidium*, and *Candida* species were found showing the desired activity. All the strains displayed S selectivity. Those strains were then re-screened and yeasts UC2387 belonging to *Rhodotorula* species was chosen for the preparation of S-1 at larger scales.

TABLE 3

| ATCC Number or other | Strain name | ATCC Number or other | Strain name |
|---|---|---|---|
| ATCC 18101 | *Rhodotorula* sp. | UC2401 | *Rhodotorula* sp. |
| ATCC 18818 | *Rhodotorula diffluens* | UC2395 | *Candida* sp. |
| ATCC 14023 | *Rhodotorula mucilaginosa* | UC2466 | *Rhodosporibium dibovstum* |
| ATCC 18813 | *Rhodotorula buffonii* | UC2461 | *Rhodotorula rubra* |
| ATCC 20804 | *Rhodotorula graminis* | UC2454 | *Rhodotrodula glutinis* |
| ATCC 10656 | *Cryptococcus flavus* | UC2447 | *Rhodotorula* sp. |
| ATCC 24010 | *Rhodotorula javanica* | UC2431 | *Sporobolomyces* sp. |
| ATCC 28954 | *Rhodotorula bacarum* | UC17612 | Unknown yeast |
| ATCC 28322 | *Rhodotorula sonckii* | UC17613 | Unknown yeast |
| ATCC 20837 | *Rhodotorula* sp. | UC2472 | *Rhodotorula rubra* |
| ATCC 20254 | *Rhodotorula* sp. | UC2471 | *Rohodorule minuta* |
| ATCC 28135 | *Rhodotorula hordea* | UC2468 | *Rhodotroula graminis* |
| ATCC 22078 | *Rhodotorula araucariae* | UC17463 | Unknown yeast |
| ATCC 10659 | *Rhodotorula glutinis* | UC16748 | Unknown yeast |
| ATCC 58914 | *Rhodotorula futronensis* | UC16508 | Unknown yeast |
| ATCC 52903 | *Rhodotorula phylloplana* | UC4229 | *Rhodosporidium sphacrocarpum* |
| ATCC 52902 | *Rhodotorula hinnulea* | UC4235 | *Rhodosporidium sphacrocarpum* |
| ATCC 52907 | *Rhodotorula armeniaca* | UC4246 | *Hansenula anomala* |
| ATCC 42713 | *Rhodotorula acuta* | UC4254 | *Candida norvegensis* |
| ATCC 32034 | *Rhodotorula pustula* | UC4265 | *Candida zeylenoides* |
| ATCC 10658 | *Rhodotorula minuta* | UC4281 | *Cryptococcus albidus* |
| ATCC 42552 | *Rhodotorula matritensis* | UC4247 | *Hanseniaspora uvarum* |
| ATCC 28983 | *Rhodotorula* sp. | UC4255 | *Rhodotorula rubra* |
| ATCC 76737 | *Rhodotorula ferulica* | UC4266 | *Candida rugosa* |
| ATCC 90775 | *Rhodotorula aurantiaca* | UC4282 | *Debaryomyces hansenii* |
| ATCC 10655 | *Rhodotorula aurantiaca* | UC4248 | *Candida parapsilosis* |
| ATCC 52823 | *Rhodotorula fujisanensis* | UC4256 | *Debaryomyces hansenii* |
| ATCC 90391 | *Rhodotorula lactosa* | UC4238 | *Saccharomuces cerevisai* |
| ATCC 32764 | *Rhodotorula aurantiaca* | UC4272 | *Candida tropicalis* |
| ATCC 32768 | *Rhodotorula graminis* | UC4288 | *Trichosporan cutaneum* |
| ATCC 52902 | *Rhodotorula nothofagi* | UC4242 | *Cryptococcus laurentii* |
| ATCC 13546 | *Cryptococcus laurentii* | UC4250 | *Candida tenius* |
| ATCC 16727 | *Rhodotorula graminis* | UC4259 | *Candida* sp. |
| ATCC 18176 | *Rhodotorula lactosa* | UC4275 | *Rhodotorula* sp. |
| ATCC 16182 | *Cystofilobasidiuminfirmominiatum* | UC4289 | *Candida raghii* |
| ATCC 886 | *Rhodotorula* sp. | UC4244 | *Rhodosporidium sphacrocarpum* |
| ATCC 22946 | *Rhodotorula fujisanensis* | UC4253 | *Candida polymorpha* |
| ATCC 22993 | *Rhodotorula ingeniosa* | UC4263 | *Rhodotorula pilimanae* |
| ATCC 22875 | *Rhodotorula hylophila* | UC4277 | *Rhodotorula glutinis* |
| ATCC 18809 | *Rhodotorula bogoriensis* | UC4294 | *Candida norvegensis* |
| ATCC 34886 | *Rhodotorula muscorum* | UC 1787 | *Aerobasidium* sp. |
| ATCC 44533 | *Rhodotorula pilati* | UC2387 | *Aerobasidium* sp. |
| ATCC 24121 | *Rhodotorula auriculariae* | UC1827 | *Bullera* sp. |
| ATCC 18820 | *Rhodotorula foliorum* | UC1846 | *Geotrichum* sp. |
| ATCC 28485 | *Pichia pastoris* | UC1281 | *Candida* sp. |
| ATCC 17697 | *Alcaligenes euntrophus* | UC1763 | *Bullera* sp. |
| ATCC 999 | *Rhodococcus rhodochrous* | UC1765 | *Aerobasidium* sp. |
| ATCC 35411 | *Lactobacillus kefir* | UC1247 | *Rhodotorula* sp. |
| ATCC 27337 | *Peptostreptococcus anaerobius* | UC1256 | *Rhodotorula* sp. |
| ATCC 26012 | *Hansenula polymorpha* | UC1264 | *Candida* sp. |
| ATCC 17798 | *Chlostridium* ps. | UC1268 | *Cryptococcus* sp. |

TABLE 3-continued

| ATCC Number or other | Strain name | ATCC Number or other | Strain name |
| --- | --- | --- | --- |
| ATCC 25619 | *Pseudomonas aureginosa* | UC1276 | *Rhodotorula* sp. |
| ATCC 23973 | *Pseudomonas putida* | UC1202 | *Rhodosporidium* sp |
| ATCC 12276 | *Aspergillus niveus* | UC1209 | *Cryptococcus* sp. |
| ATCC 10436 | *Penicillum decumbens* | UC1213 | *Cryptococcus* sp. |
| ATCC 66815 | *Thorulaspora* sp. | UC1235 | *Candida* sp. |
| ATCC7159 | *Beauveria sulfurences* | UC1240 | *Cryptococcus* sp. |
| ATCC 21766 | *Corynebacterium dyoxidans* | UC1184 | *Candida* sp. |
| ATCC 33305 | *Acinetobacter* sp. | UC1779 | *Aerobasidium* sp. |
| ATCC 1207a | *Mucor circinelloides* | UC1185 | *Rhodotroula* sp. |
| ATCC 22792 | *Dipodascus uninucleatus* | UC1190 | *Rhodotroula* sp. |
| ATCC 12975 | *Rhodococcus fascians* | UC1192 | *Rhodosporidium* sp |
| ATCC 7924 | *Mucor racemosum* | UC1195 | *Candida* sp. |
| ATCC 11048 | *Rhodococcus erythropolis* | UC5113 | *Aerobasidium mansonii* |
| ATCC 9692 | *Mucor rammanianus* | UC5098 | *Cryptococcus laurentii* var *laurentii* |
| ATCC 29670 | *Rhodococcus rhodochrous* | UC5084 | *Cryptococcus laurentii* var *laurentii* |
| NRRL Y-164 | *Schizosaccaromyces pombe* | UC4317 | *Candida tenius* |
| ATCC 10613 | *S. uvarum* | UC4310 | *Rhodotorula* sp. |
| ATCC35047 | *Thermoanaerobacter brokii* | UC5110 | *Candida guillermondii* |
| ATCC 10788 | *Rhodotorula toruloides* | UC5093 | *Cryptococcus laurentii* var *laurentii* |
| ATCC 35091 | *Sulfolobus solfataricus* | UC4327 | *Rhodotorula rubra* |
| ATCC 8527 | *Clostridium kluyver*-anaerobic | UC4316 | *Candida curvata* |
| ATCC 14692 | *Neurospora crassa* | UC4309 | *Rhodotorula rubra* |
| ATCC 16617 | *Yarrowia lipolytica* | UC5103 | *Candida* sp. |
| ATCC 21664 | *Rhodococcus* sp. | UC5089 | *Hanseniaspora uvarum* |
| ATCC 38191 | *Mortierella ramanniana* | UC4324 | *Cryptococcus* sp. |
| ATCC 10640 | *Kloeckera corticis* | UC4315 | *Candida* sp. |
| ATCC 10679 | *T. variabilis* | UC4305 | *Candida tenius* |
| ATCC 39213 | *Pseudomonas putida* | UC5101 | *Matschinkowia bucuspibata* |
| ATCC 49097 | *Bacillus simplex* | UC5088 | *Hansenula anomala* |
| UC 2390 | *Rhodotorula* Sp. | UC4321 | *Cryptococcus albidus* var *albidus* |
| UC2387 | *Rhodotorula* Sp. | UC4313 | *candida lipolytica* |
| UC2386 | *Rhodotorula minuta* | UC4304 | *Candida tropicalis* |
| UC2385 | *Cryococcus* sp. | UC5100 | *Candida norvegensis* |
| UC2371 | *Candida* sp. | UC5087 | *Candida krusei* |
| UC2419 | *Candida* sp. | UC4319 | *Torulobsis candida* |
| UC2411 | *Rhodotorula* sp. | UC4312 | *Trichosporum cutaneum* |
| UC2405 | *Debaryomyces* sp. | UC4297 | *Sacharomyces laurentii* |
| UC4272 | Unknown yeast | UC4289 | Unknown yeast |
| UC4288 | Unknown yeast | UC4244 | Unknown yeast |
| UC4242 | Unknown yeast | UC4253 | Unknown yeast |
| UC4250 | Unknown yeast | UC4263 | Unknown yeast |
| UC4259 | Unknown yeast | UC4277 | Unknown yeast |
| UC4275 | Unknown yeast | UC4294 | Unknown yeast |

Large-Scale Procedure for the Preparation of (1S)-1-(2,6-dichloro-3-fluorophenyl)ethanol (S-1) by Reduction of 1-(2,6-dichloro-3-fluorophenyl)ethanone Using *Rhodutorula* sp. strain Y2-UC2387

Bio-reduction of 1-(2,6-dichloro-3-fluorophenyl)ethanone to (1S)-1-(2,6-dichloro-3-fluorophenyl)ethanol (S-1) using *Rhodutorula* sp. strain Y2-UC2387 was performed according to Scheme 6 as follows below.

Scheme 6

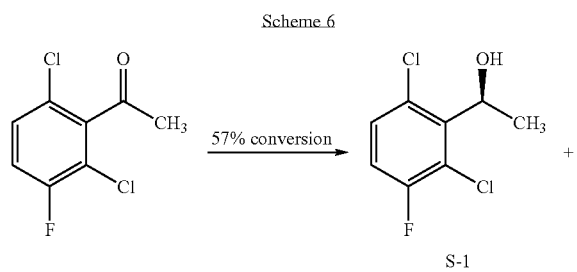

-continued

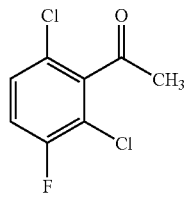

A two-stage fermentation procedure was set up where pre-culture (first stage) was grown from fresh inoculum (colony picked from agar plate) in shake flasks for 2 days. The second stage culture was started by adding pre-culture to fresh media (1/50-1/100 dilution) and the resulting culture was grown for 1 day before substrate was added from a 10% ethanol solution. YM media (Difco media 271120) was used for both liquid cultures as well as the agar based plates. For the reduction of 2 g (9.6 mmol) of 1-(2,6-dichloro-3-fluorophenyl)ethanone, a 1 L preparation was needed. The first stage culture contained 10 mL YM and the whole culture was used to inoculate the second stage culture (1 L). After growing for 3 days, substrate was added neat and reaction stirred for 7 days. Both the conversion of 1-(2,6-dichloro-3-fluorophenyl)ethanone to the desired isomer of the alcohol S-1 and ee of S-1 were monitored by RP-HPLC. The reaction was stopped after 57% conversion was reached when yeast cells were removed by centrifugation at 5,000 rpm. The remaining starting material and the desired product were recovered by extraction (three times with 0.5 volumes of ethyl acetate).

Studies on the Maximum Substrate Loads and Recycling of Yeast Cells

Substrate concentration in the range of 1-20 g/L was tested, and 2.5 g/L chosen because it allowed the best space-time yield (~0.5 g/L/d) corresponding to a product formation rate of 0.1 g per gram of microorganism per day. The yields of isolated product are in the range from 50 to 100%. The poor solubility of the precursor in water <2.5 g/L prevents the use of higher substrate loads. Non ionic XAD resins (produced by Rohm and Hass) known to adsorb organic compounds (according to a paper by D'Arrigo, et al, *Tetrahedron: Asymmetry*, 1997, vol. 8, pp. 2375-2379) could be used for the entrapment of the substrate or product (mostly to provide a slow release of substrate and to avoid toxicity of substrate to cells or enzyme inhibition). This technique allows the use of substrate loads of 20 g/L or higher.

Cells immobilized in calcium alginate according to the procedure by Rotthaus, et al, *Tetrahedron*, 2002, vol. 58, pp. 7291-93, proved to be a practical solution for the recycling and better use of the catalyst. The entrapped yeast cells were more resistant to mechanical stress and at the same time, significant improvements in the recovery of products were observed. Substrate loads similar to the ones observed with whole cells were also seen.

Screening of the Commercially Available Enzymes

The screening for enzymes capable of doing the enantioselective reduction of 1-(2,6-dichloro-3-fluorophenyl)ethanone was carried out as follows. 27 different ketone reductases (purchased from Biocatalytics, Inc as a KRED-M27 KIT), as well as 4 alcohol dehydrogenases (horse liver alcohol dehydrogenase (HLADH), yeast alcohol dehydrogenase, *Thermoanaerobium brokii* alcohol dehydrogenase and *Lactobacillus kefir* alcohol dehydrogenase) available from Sigma Aldrich, were tested. The Kred enzyme reactions were performed at 1 mg/mL substrate load and using NADPH as the reducing agent. Alcohol dehydrogenases were tested using both NADH and NADPH. Only horse liver alcohol dehydrogenase (HLADH) catalyzed the selective reduction of 1-(2, 6-dichloro-3-fluorophenyl)ethanone to afford (S)-1 according to Scheme 7.

Scheme 7

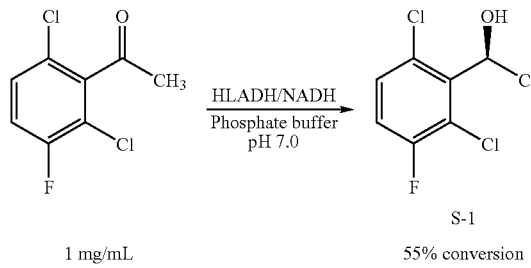

1 mg/mL → HLADH/NADH, Phosphate buffer pH 7.0 → S-1, 55% conversion +

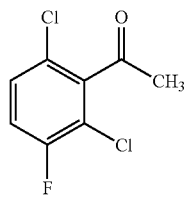

-continued

HLADH has been previously reported for the reduction of multiple substrates (it acts as an E3 type ADH according to Nakamura, et al, *Tetrahedron asymmetry*, 2003, vol. 14, pp. 2659-2681) following the prelog's rule (Prelog, V, *Pure App. Chem.*, 1964, vol. 9, 119).

Table 4 contains the substrate to enzyme (S:E) ratios evaluated.

TABLE 4

| Ratio | Conversion (%) | | |
|---|---|---|---|
| S:E | NADPH | NAD | Rx time(h) |
| 1:1 | 6 | 15 | 18 |
| 1:2 | 13 | 25 | 18 |
| 1:5 | 20 | 41 | 18 |
| 1:10 | 42 | 55 | 64 |

Compound S-1
(1S)-1-(2,6-dichloro-3-fluorophenyl)ethanol

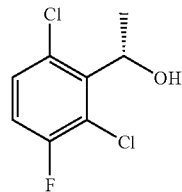

Compound S-1 was purified from the starting material ketone by flash chromatography (eluting with 15→20% EtOAc in hexanes) to give compound S-1 as a colorless oil (229.8 mg; 1.1 mmol); SFC-MS: 100% ee. $^1$H NMR (400 MHz, MeOD) ? ppm 1.58 (d, J=7.1 Hz, 3H) 5.61 (q, J=6.8 Hz, 1H) 7.14 (t, J=8.6 Hz, 1H) 7.35 (dd, J=9.0, 4.9 Hz, 1H).

Example 3

Use of (1S)-1-(2,6-Dichloro-3-Fluorophenyl)Ethanol in the Synthesis of Human Hepatocyte Growth Factor Receptor Tyrosine Kinase Inhibitors (1S)-1-(2,6-dichloro-3-fluorophenyl)ethanol was used as an intermediate in chiral synthesis of human hepatocyte growth factor receptor tyrosine kinase inhibitors according to Scheme 8 and synthetic procedures described below.

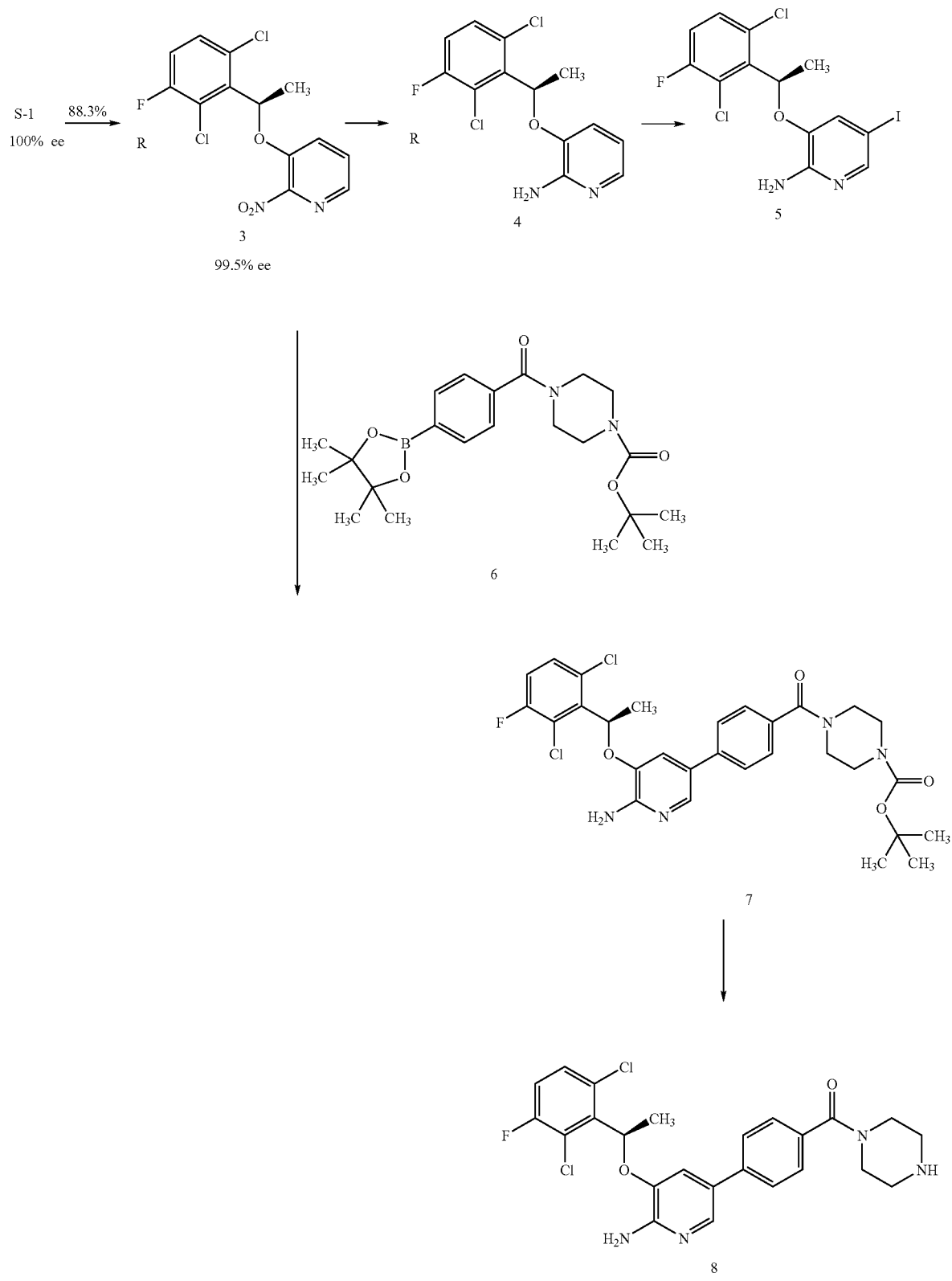

Compound 3

3-[(1R)-1-(2,6-dichloro-3-fluorophenyl)ethoxy]-2-nitropyridine

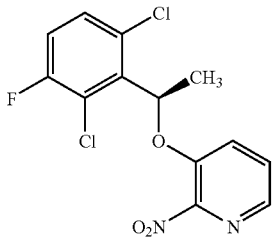

3-Hydroxy-2-nitropyridine (175 mg, 1.21 mmol), triphenylphosphine (440 mg, 1.65 mmol) were added sequentially to a stirred solution of S-1 (229.8 mg, 1.1 mmol) in THF (10 mL) under a nitrogen atmosphere. The reaction mixture was maintained at room temperature for 1 h and then diisopropyl azo-dicarboxylate (0.34 mL, 1.65 mmol) was added at 0° C. The mixture was stirred for an additional 12 h. The reaction mixture was evaporated under vacuum to give an oil. The residue was purified by flash chromatography (eluting with 20→25% EtOAc in hexanes) to give compound 3 as a white solid (321.5 mg; 0.97 mmol; 88.3% yield); MS (APCI) $(M+H)^+$ 331; SFC-MS: 99.5% ee. $^1$H NMR (400 MHz, CHLOROFORM-D) δ ppm 1.85 (d, J=6.6 Hz, 3H) 6.10 (q, J=6.6 Hz, 1H) 7.04-7.13 (m, 1H) 7.21 (dd, J=8.5, 1.14 Hz, 1H) 7.30 (dd, J=9.0, 4.9 Hz, 1H) 7.37 (dd, J=8.6, 4.6 Hz, 1H) 8.04 (dd, J=4.6, 1.3 Hz, 1H).

Compound 4

3-[(1R)-1-(2,6-dichloro-3-fluorophenyl)ethoxy]pyridin-2-amine

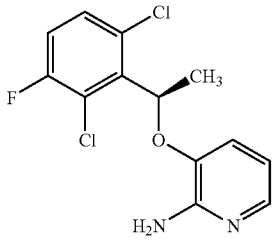

Iron (365 mg) was added to a stirred solution of compound 3 (321 mg, 0.97 mmol) in a mixture of EtOH (2 mL) and 2M HCl (0.2 mL) at 0° C. The resulting solution was heated to 85° C. for 2 h. Celite (0.5 g) was added to the cooled reaction mixture. This mixture was filtered over a bed of celite and evaporated to give compound 4 as a dark oil. MS (APCI) $(M+H)^+$ 301. Compound 4 was used in the next step reaction without further purification.

Compound 5

3-[(1R)-1-(2,6-dichloro-3-fluorophenyl)ethoxy]-5-iodopyridin-2-amine

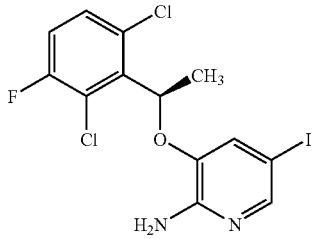

Periodic acid (60 mg, 0.24 mmol), iodine (130 mg, 0.5 mmol), and sulfuric acid (0.03 mL) were added sequentially to a stirred solution of compound 4 (0.97 mmol) in a mixture of acetic acid (3 mL) and $H_2O$ (0.5 mL). The resulting solution was heated to 80° C. for 5 h. The cooled reaction mixture was quenched with $Na_2SO_3$ (80 mg) and basicified with sat. $Na_2CO_3$ (2×100 mL) to pH 7. $CH_2Cl_2$ (2×50 mL) was added to extract the aqueous solution. The combined organic layers were dried over $Na_2SO_4$ then filtered and concentrated under vacuum. The residue was purified by flash chromatography (eluting with 35→40% EtOAc in hexanes) to give compound 5 as a yellow oil (254 mg; 0.6 mmol; 61.6% yield); MS (APCI) $(M+H)^+$ 426. $^1$H NMR (400 MHz, chloroform-D) δ ppm 1.81 (d, J=6.8 Hz, 3H) 4.86 (s, 2H) 5.98 (q, J=6.57 Hz, 1H) 6.96 (d, J=1.5 Hz, 1H) 7.08 (dd, J=9.0, 8.0 Hz, 1H) 7.31 (dd, J=8.8, 4.8 Hz, 1H) 7.78 (d, J=1.8 Hz, 1H).

Compound 6 tert-Butyl 4-[4-(4,4,5,5-tetramethyl-1,3,2-dioxaborolan-2-yl)benzoyl]piperazine-1-carboxylate

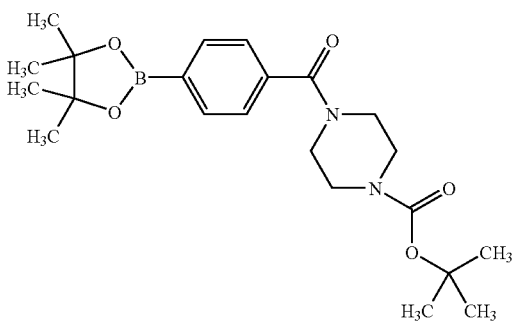

1,1'-carbonyl-diimidazole (360 mg, 2.2 mmol) was added to a solution of 4-(4,4,5,5-tetramethyl-1,3,2-dioxaborolan-2-yl)benzoic acid (515 mg, 2 mmol) in $CH_2Cl_2$ (50 mL) under inert atmosphere. The reaction mixture was stirred at room temperature for 30 min and then tert-butyl-1-piperazine-carboxylate (390 mg, 2 mmol) was added. The resulting suspension was stirred for 12 h under inert atmosphere. The mixture was poured into $H_2O$ (50 mL) to stir and $CH_2Cl_2$ (2×50 mL) was added to extract the aqueous solution. The combined organic layers were dried, filtered and concentrated to give a colorless oil residue. The residue was purified by flash chromatography (eluting with 20→25% EtOAc in hexanes) to give compound 6 as a white solid (461 mg; 1.1 mmol; 55.4% yield); MS (APCI) (M+H)+ 417. ¹H NMR (400 MHz, chloroform-D) δ ppm 1.34 (s, 12H) 1.45 (s, 9H) 3.26-3.42 (m, 4H) 3.44-3.56 (m, 2 H) 3.66-3.89 (m, 2H) 7.37 (d, J=8.1 Hz, 2H) 7.84 (d, J=8.1 Hz, 2H).

Compound 7
tert-Butyl 4-(4-(6-amino-5-[(1R)-1-(2,6-dichloro-3-fluorophenyl)ethoxy]pyridin-3-yl)benzoyl)piperazine-1-carboxylate

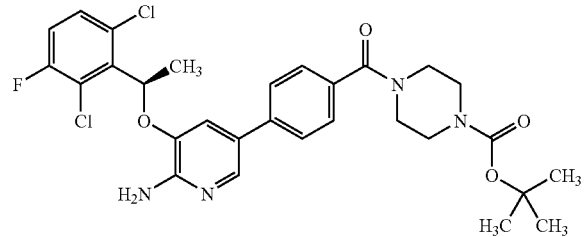

Compound 6 (300 mg, 0.72 mmol) was added to a solution of compound 5 (254 mg, 0.6 mmol) in 7 mL of DME (ethylene glycoldimethyl ether). The mixture was purged with nitrogen several times and then dichlorobis(triphenylphsophino) palladium (II) (50 mg, 0.06 mmol) was added. Sodium carbonate (200 mg, 1.8 mmol) in 1.5 mL of H₂O was added to the reaction mixture and the resulting solution was heated to 85° C. for 12 h. Water (50 mL) was added to the reaction mixture to quench the reaction. EtOAc (2×50 mL) was then added to extract the aqueous solution. The combined EtOAc layer was dried, filtered, and evaporated to give a brown yellow oil residue. The residue was purified by silica gel chromatography (eluting with 75→80% EtOAc in hexanes) to give compound 7 as a white solid (255.5 mg; 0.43 mmol; 72.9% yield); MS (APCI) (M+H)+ 589. ¹H NMR (400 MHz, chloroform-D) δ ppm 1.45 (s, 9H) 1.85 (d, J=6.6 Hz, 3H) 4.92 (s, 2H) 6.10 (q, J=6.8 Hz, 1H) 6.97 (d, J=1.8 Hz, 1H) 7.01-7.10 (m, 1H) 7.29 (dd, J=9.0, 4.9 Hz, 1H) 7.36-7.42 (m, 3H) 7.58-7.64 (m, 1H) 7.87 (d, J=1.5 Hz, 1H).

Compound 8
3-[(1R)-1-(2,6-dichloro-3-fluorophenyl)ethoxy]-5-[4-(piperazin-1-ylcarbonyl)phenyl]pyridin-2-amine

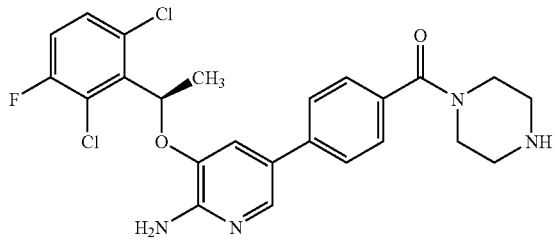

Hydrochloric acid (1.3 mL, 4.8 mmol) was added to a solution of compound 7 in ethanol (10 mL). The reaction mixture was stirred at room temperature for 12 h and then was evaporated under vacuum to give an oil. The residue was purified by flash chromatography (eluting with 25→40% CH₃OH in EtOAc) to give compound 8 as a white solid (180.4 mg; 0.37 mmol; 85.2% yield); MS (APCI) (M+H)+ 489; SFC-MS: 100% ee. ¹H NMR (400 MHz, MeOD) δ ppm 1.88 (d, J=6.8 Hz, 3H) 2.92-3.21 (m, 4H) 3.58-4.07 (m, 4H) 6.21 (q, J=6.8 Hz, 1H) 7.02 (d, J=1.8 Hz, 1H) 7.18-7.27 (m, 1H) 7.41-7.45 (m, 1H) 7.46 (s, 4H) 7.78 (d, J=1.8 Hz, 1H). Anal. Calcd for C₂₄H₂₃Cl₂FN₄O₂.2HCl.1.25H₂O C: 49.29, H, 4.74; N, 9.58. Found C, 49.53; H, 4.82, N, 9.29.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

The entire disclosure of patents and patent applications and non-patent publications cited in the present specification is incorporated by reference.

We claim:

1. (1S)-1-(2,6-dichloro-3-fluorophenyl)ethanol in an enantiomerically pure form.

2. (1S)-1-(2,6-dichloro-3-fluorophenyl)ethanol having an enantiomeric purity equal to at least 80%.

3. (1S)-1-(2,6-dichloro-3-fluorophenyl)ethanol as defined in claim 2 having an enantiomeric purity equal to at least 95%.

4. (1S)-1-(2,6-dichloro-3-fluorophenyl)ethanol as defined in claim 2 having an enantiomeric purity equal to at least 97%.

5. A composition comprising (1S)-1-(2,6-dichloro-3-fluorophenyl)ethanol substantially free from its corresponding R-enantiomer.

6. A composition comprising (1S)-1-(2,6-dichloro-3-fluorophenyl)ethanol that is at least 80% free of (1R)-1-(2,6-dichloro-3-fluorophenyl)ethanol.

7. The composition as defined in claim 6 comprising (1S)-1-(2,6-dichloro-3-fluorophenyl)ethanol that is at least 95% free of(1R)-1-(2,6-dichloro-3-fluorophenyl)ethanol.

8. The composition as defined in claim 6 comprising (1S)-1-(2,6-dichloro-3-fluorophenyl)ethanol that is at least 97% free of(1R)-1-(2,6-dichloro-3-fluorophenyl)ethanol.

9. A method for preparing the product of claim 1, (1S)-1-(2,6-dichloro-3-fluorophenyl)ethanol, comprising the steps of:

contacting of a mixture of enantiomeric 1-(2,6-dichloro-3-fluorophenyl)ethanol esters of formula (I):

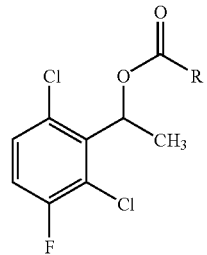

wherein R is hydrogen, C₁-C₂₀-alkyl, C₃-C₈-cycloalkyl, C₆-C₁₄-aryl, C₇-C₁₅-arylalkyl, C₁-C₂₀-alkoxy, C₁-C₂₀-alkylamino, wherein said hydrocarbon radicals can optionally be monosubstituted or polysubstituted with hydroxyl, formyl, oxy, C₁-C₆-alkoxy, carboxy, mercapto, sulpho, amino, C₁-C₆-alkylamino or nitro or halogen, with an enzyme selected from the group consisting of Amano D (R. delemar lipase), Amano AY (C. rugosa lipase), Amano F (R. oryzae lipase) and pig liver esterase in an aqueous solution, an organic solvent, or a mixture of organic and aqueous solvents wherein only (R)-enantiomer is selectively hydrolyzed to give a mixture of (1R)-1-(2,6-dichloro-3-fluorophenyl)ethanol and a (1S)-1-(2,6-dichloro-3-fluorophenyl)ethanol ester;

converting the mixture of (1R)-1-(2,6-dichloro-3-fluorophenyl)ethanol and the (1S)-1-(2,6-dichloro-3-fluorophenyl)ethanol ester to (1S)-1-(2,6-dichloro-3-fluorophenyl)ethanol; and recovering (1S)-1-(2,6-dichloro-3-fluorophenyl)ethanol.

10. The method according to claim 9, wherein the converting step comprises:

a) reacting (1R)-1-(2,6-dichloro-3-fluorophenyl)ethanol in the mixture of (1R)-1-(2,6-dichloro-3-fluorophenyl)ethanol and the (1S)-1-(2,6-dichloro-3-fluorophenyl)ethanol ester with an organic sulfonyl halide in an aprotic solvent to form a mixture of an organic sulfonic acid ester of (1R)-1-(2,6-dichloro-3-fluorophenyl)ethanol and the (1S)-1-(2,6-dichloro-3-fluorophenyl)ethanol ester;

b) further reacting the organic sulfonic acid ester of (1R)-1-(2,6-dichloro-3-fluorophenyl)ethanol in the mixture of the organic sulfonic acid ester of (1R)-1-(2,6-dichloro-3-fluorophenyl)ethanol and the (1S)-1-(2,6-dichloro-3-fluorophenyl)ethanol ester with an alkali metal salt of an aliphatic carboxylic acid in an aprotic solvent to form a mixture of an aliphatic carboxylic acid ester of (1S)-1-(2,6-dichloro-3-fluorophenyl)ethanol and the (1S)-1-(2,6-dichloro-3-fluorophenyl)ethanol ester; and c) transforming the mixture of the aliphatic carboxylic acid ester of (1S)-1-(2,6-dichloro-3-fluorophenyl)ethanol and the (1S)-1-(2,6-dichloro-3-fluorophenyl)ethanol ester into (1S)-1-(2,6-dichloro-3-fluorophenyl)ethanol.

11. The method according to claim 10, wherein the transforming step c) comprises:

solvolyzing the mixture of the aliphatic carboxylic acid ester of (1S)-1-(2,6-dichloro-3-fluorophenyl)ethanol and the (1S)-1-(2,6-dichloro-3-fluorophenyl)ethanol ester in an alcoholic or aqueous solvent in the presence of a basic substance to form (1S)-1-(2,6-dichloro-3-fluorophenyl)ethanol.

12. The method according to claim 11, wherein in the transforming step c) the mixture of the aliphatic carboxylic acid ester of (1S)-1-(2,6-dichloro-3-fluorophenyl)ethanol and the (1S)-1-(2,6-dichloro-3-fluorophenyl)ethanol ester is solvolyzed in methanol in the presence of sodium methoxide to form (1S)-1-(2,6-dichloro-3-fluorophenyl)ethanol.

13. The method according to claim 12, wherein:

R is methyl;

in the reacting step a) the organic sulfonyl halide is methanesulfonyl chloride, the aprotic solvent is pyridine;

in the reacting step b) the alkali metal salt of aliphatic carboxylic acids is potassium acetate, the aprotic solvent is dimethylformamide.

14. The method according to claim 13, wherein the enzyme is used in an amount of 0.1 to 100 parts by weight based on 100 parts by weight of the mixture of enantiomeric 1-(2,6-dichloro-3-fluorophenyl)ethanol esters.

15. The method according to claim 9, wherein the contacting step of the mixture of enantiomeric 1-(2,6-dichloro-3-fluorophenyl)ethanol esters with the biocatalyst is carried out in an aqueous solution at 0 to 60° C. with maintenance of pH at 4 to 12.

16. The method according to claim 13, wherein the biocatalyst is pig liver esterase.

* * * * *